(12) United States Patent
Little, II et al.

(10) Patent No.: US 6,355,616 B1
(45) Date of Patent: Mar. 12, 2002

(54) DERIVATIVE COMPOUNDS DERIVED FROM OR BASED ON BACTERICIDAL/ PERMEABILITY-INCREASING PROTEIN

(75) Inventors: Roger G. Little, II, Benicia; Jong-Jye Lin, Hercules; J. G. Kinyua Gikonyo, Berkeley, all of CA (US)

(73) Assignee: Xoma (US) Technology Ltd., Berkeley, CA (US)

( * ) Notice: Subject to any disclaimer, the term of this patent is extended or adjusted under 35 U.S.C. 154(b) by 0 days.

(21) Appl. No.: 09/344,541

(22) Filed: Jun. 25, 1999

(51) Int. Cl.[7] .................. A61K 38/07; A61K 38/08; A61K 38/10; C07K 5/103; C07K 7/06
(52) U.S. Cl. .............. 514/14; 514/15; 514/16; 514/17; 514/18; 530/327; 530/328; 530/329; 530/330; 530/345
(58) Field of Search ................. 514/7, 14, 15, 514/16, 17, 18; 530/327, 328, 329, 330, 345

(56) References Cited

U.S. PATENT DOCUMENTS 5,652,332 A  7/1997  Little et al. ............... 530/324
5,858,974 A * 1/1999  Little, II et al. ............. 514/12

FOREIGN PATENT DOCUMENTS

| WO | WO 96/08509 | 3/1996 |
| WO | WO 97/04008 | 2/1997 |
| WO |    97/04008 | * 2/1997 |
| WO | WO 97/09344 | 3/1997 |

OTHER PUBLICATIONS

Little, et al., Functional Domains of Recombinant Bactericidal/Permeability Increasing Protein (rBPI23), *The Journal of Biological Chemistry*, 269(3):1865–1872 (1994).

* cited by examiner

*Primary Examiner*—Jeffrey E. Russel
(74) *Attorney, Agent, or Firm*—McAndrews, Held & Malloy, Ltd.

(57) ABSTRACT

The present invention relates generally to derivatized antifungal compounds that are peptide-based constructs derived from or based on subsequences of Domain III (amino acids 142–169) of bactericidal/permeability-increasing protein (BPI) and in vivo or in vitro uses of such compounds.

17 Claims, No Drawings

SEQUENCE LISTING

<160> NUMBER OF SEQ ID NOS: 61

<210> SEQ ID NO 1
<211> LENGTH: 10
<212> TYPE: PRT
<213> ORGANISM: derived from human
<220> FEATURE:
<223> OTHER INFORMATION: XMP.365
<221> NAME/KEY: SITE
<222> LOCATION: (1)..(10)
<223> OTHER INFORMATION: Positions 1-10 are D-Amino Acids
<221> NAME/KEY: SITE
<222> LOCATION: (10)
<223> OTHER INFORMATION: AMIDATION=The C-terminus is Amidated

```
<400> SEQUENCE: 1

Lys Trp Leu Ile Gln Leu Phe His Lys Lys
 1               5                  10

<210> SEQ ID NO 2
<211> LENGTH: 10
<212> TYPE: PRT
<213> ORGANISM: derived from human
<220> FEATURE:
<223> OTHER INFORMATION: XMP.366
<221> NAME/KEY: SITE
<222> LOCATION: (1)
<223> OTHER INFORMATION: Position 1 is derivatized at the  alpha-amino
      with:  acetyl
<221> NAME/KEY: SITE
<222> LOCATION: (1)..(10)
<223> OTHER INFORMATION: Positions 1-10 are D-Amino Acids
<221> NAME/KEY: SITE
<222> LOCATION: (10)
<223> OTHER INFORMATION: AMIDATION=The C-terminus is Amidated

<400> SEQUENCE: 2

Lys Trp Leu Ile Gln Leu Phe His Lys Lys
 1               5                  10

<210> SEQ ID NO 3
<211> LENGTH: 10
<212> TYPE: PRT
<213> ORGANISM: derived from human
<220> FEATURE:
<223> OTHER INFORMATION: XMP.416
<221> NAME/KEY: SITE
<222> LOCATION: (1)
<223> OTHER INFORMATION: Position 1 is derivatized at the alpha-amino
      with: 7- amino-heptylcarbonyl
<221> NAME/KEY: SITE
<222> LOCATION: (1)..(10)
<223> OTHER INFORMATION: Positions 1-10 are D-Amino Acids
<221> NAME/KEY: SITE
<222> LOCATION: (10)
<223> OTHER INFORMATION: AMIDATION=The C-terminus is Amidated

<400> SEQUENCE: 3

Lys Trp Leu Ile Gln Leu Phe His Lys Lys
 1               5                  10

<210> SEQ ID NO 4
<211> LENGTH: 12
<212> TYPE: PRT
<213> ORGANISM: derived from human
<220> FEATURE:
<223> OTHER INFORMATION: XMP.424
<221> NAME/KEY: SITE
<222> LOCATION: (4)
<223> OTHER INFORMATION: Position 4 is 3,4-difluoro Phe substituted
<221> NAME/KEY: SITE
<222> LOCATION: (9)
<223> OTHER INFORMATION: Position 9 is 3,4-difluoro Phe substituted
<221> NAME/KEY: SITE
<222> LOCATION: (1)..(12)
<223> OTHER INFORMATION: Positions 1-12 are L-amino acids
<221> NAME/KEY: SITE
<222> LOCATION: (12)
<223> OTHER INFORMATION: AMIDATION=The C-terminus is Amidated

<400> SEQUENCE: 4

Lys Val Gly Phe Leu Ile Gln Leu Phe His Lys Lys
 1               5                  10

<210> SEQ ID NO 5
<211> LENGTH: 12
```

```
<212> TYPE: PRT
<213> ORGANISM: derived from human
<220> FEATURE:
<223> OTHER INFORMATION: XMP.446
<221> NAME/KEY: SITE
<222> LOCATION: ()..(12)
<223> OTHER INFORMATION: Positions 1-12 are D-amino acids
<221> NAME/KEY: SITE
<222> LOCATION: (12)
<223> OTHER INFORMATION: AMIDATION=The C=terminus is Amidated

<400> SEQUENCE: 5

Lys Val Gly Trp Leu Ile Gln Leu Phe His Lys Lys
  1               5                  10

<210> SEQ ID NO 6
<211> LENGTH: 14
<212> TYPE: PRT
<213> ORGANISM: derived from human
<220> FEATURE:
<223> OTHER INFORMATION: XMP.447
<221> NAME/KEY: SITE
<222> LOCATION: (6)..(7)
<223> OTHER INFORMATION: Positions 6 and 7 are L-amino acids
<221> NAME/KEY: SITE
<222> LOCATION: (1)..(5)
<223> OTHER INFORMATION: Positions 1-5 are D-amino acids
<221> NAME/KEY: SITE
<222> LOCATION: (8)..(14)
<223> OTHER INFORMATION: Positions 8-14 are D-amino acids
<221> NAME/KEY: SITE
<222> LOCATION: (14)
<223> OTHER INFORMATION: AMIDATION=The C-terminus is Amidated

<400> SEQUENCE: 6

Lys Ser Lys Val Gly Val Ala Ile Gln Leu Phe His Lys Lys
  1               5                  10

<210> SEQ ID NO 7
<211> LENGTH: 9
<212> TYPE: PRT
<213> ORGANISM: derived from human
<220> FEATURE:
<223> OTHER INFORMATION: XMP.459
<221> NAME/KEY: SITE
<222> LOCATION: (4)
<223> OTHER INFORMATION: Position 4 is para-fluoro Phe substituted
<221> NAME/KEY: SITE
<222> LOCATION: (9)
<223> OTHER INFORMATION: Position 9 is para-fluoro Phe substituted
<221> NAME/KEY: SITE
<222> LOCATION: (1)..(9)
<223> OTHER INFORMATION: Positions 1-9 are L-amino acids
<221> NAME/KEY: SITE
<222> LOCATION: (9)
<223> OTHER INFORMATION: AMIDATION=The C-terminus is amidated

<400> SEQUENCE: 7

Lys Val Gly Phe Leu Ile Gln Leu Phe
  1               5

<210> SEQ ID NO 8
<211> LENGTH: 12
<212> TYPE: PRT
<213> ORGANISM: derived from human
<220> FEATURE:
<223> OTHER INFORMATION: XMP.466
<221> NAME/KEY: SITE
<222> LOCATION: (1)
<223> OTHER INFORMATION: Position 1 is a D-amino acid
<221> NAME/KEY: SITE
<222> LOCATION: (2)..(12)
<223> OTHER INFORMATION: Positions 2-12 are L-amino acids
```

```
<221> NAME/KEY: SITE
<222> LOCATION: (12)
<223> OTHER INFORMATION: AMIDATION=The C-terminus is Amidated

<400> SEQUENCE: 8

Lys Val Gly Trp Leu Ile Gln Leu Phe His Lys Lys
 1               5                  10

<210> SEQ ID NO 9
<211> LENGTH: 12
<212> TYPE: PRT
<213> ORGANISM: derived from human
<220> FEATURE:
<223> OTHER INFORMATION: XMP.475
<221> NAME/KEY: SITE
<222> LOCATION: (11)
<223> OTHER INFORMATION: Position 11 is a D-amino acid
<221> NAME/KEY: SITE
<222> LOCATION: (1)..(10)
<223> OTHER INFORMATION: Positions 1-10 are L-amino acids
<221> NAME/KEY: SITE
<222> LOCATION: (12)
<223> OTHER INFORMATION: Position 12 is L-amino acid
<221> NAME/KEY: SITE
<222> LOCATION: (12)
<223> OTHER INFORMATION: AMIDATION=The C-terminus is Amidated

<400> SEQUENCE: 9

Lys Val Gly Trp Leu Ile Gln Leu Phe His Lys Lys
 1               5                  10

<210> SEQ ID NO 10
<211> LENGTH: 9
<212> TYPE: PRT
<213> ORGANISM: derived from human
<220> FEATURE:
<223> OTHER INFORMATION: XMP.486
<221> NAME/KEY: SITE
<222> LOCATION: (1)
<223> OTHER INFORMATION: Position 1 is derivatized at the alpha-amino
     with: 2- pyrazine carbonyl
<221> NAME/KEY: SITE
<222> LOCATION: (1)..(9)
<223> OTHER INFORMATION: Positions 1-9 are D-Amino Acids
<221> NAME/KEY: SITE
<222> LOCATION: (9)
<223> OTHER INFORMATION: AMIDATION=The C-terminus is Amidated

<400> SEQUENCE: 10

Lys Trp Leu Ile Gln Leu Phe His Lys
 1               5

<210> SEQ ID NO 11
<211> LENGTH: 10
<212> TYPE: PRT
<213> ORGANISM: derived from human
<220> FEATURE:
<223> OTHER INFORMATION: XMP.488
<221> NAME/KEY: SITE
<222> LOCATION: (1)
<223> OTHER INFORMATION: Position 1 is derivatized at the alpha-amino
     with: fluorescein
<221> NAME/KEY: SITE
<222> LOCATION: (1)..(10)
<223> OTHER INFORMATION: Positions 1-10 are D-Amino Acids
<221> NAME/KEY: SITE
<222> LOCATION: (10)
<223> OTHER INFORMATION: AMIDATION=The C-terminus is Amidated

<400> SEQUENCE: 11

Lys Trp Leu Ile Gln Leu Phe His Lys Lys
 1               5                  10
```

<210> SEQ ID NO 12
<211> LENGTH: 10
<212> TYPE: PRT
<213> ORGANISM: derived from human
<220> FEATURE:
<223> OTHER INFORMATION: XMP.489
<221> NAME/KEY: SITE
<222> LOCATION: (1)
<223> OTHER INFORMATION: Position 1 is derivatized at the alpha-amino
      with: acetyl
<221> NAME/KEY: SITE
<222> LOCATION: (10)
<223> OTHER INFORMATION: Position 10 is derivatized at the carboxy
      terminus with: 2-(N-fluoroscein)diaminopropylamide
<221> NAME/KEY: SITE
<222> LOCATION: (1)..(10)
<223> OTHER INFORMATION: Positions 1-10 are D-Amino Acids

<400> SEQUENCE: 12

Lys Trp Leu Ile Gln Leu Phe His Lys Lys
 1               5                  10

<210> SEQ ID NO 13
<211> LENGTH: 10
<212> TYPE: PRT
<213> ORGANISM: derived from human
<220> FEATURE:
<223> OTHER INFORMATION: XMP.492
<221> NAME/KEY: SITE
<222> LOCATION: ()..(10)
<223> OTHER INFORMATION: Positions 1-10 are D-amino acids
<221> NAME/KEY: SITE
<222> LOCATION: ()
<223> OTHER INFORMATION: Position 1 is derivatized with: 2-aminoethyl
      carbonyl
<221> NAME/KEY: SITE
<222> LOCATION: (10)
<223> OTHER INFORMATION: AMIDATION=The C-terminus is Amidated

<400> SEQUENCE: 13

Lys Trp Leu Ile Gln Leu Phe His Lys Lys
 1               5                  10

<210> SEQ ID NO 14
<211> LENGTH: 10
<212> TYPE: PRT
<213> ORGANISM: derived from human
<220> FEATURE:
<223> OTHER INFORMATION: XMP.493
<221> NAME/KEY: SITE
<222> LOCATION: (1)..(10)
<223> OTHER INFORMATION: Positions 1-10 are D-amino acids
<221> NAME/KEY: SITE
<222> LOCATION: (1)
<223> OTHER INFORMATION: Position 1 is derivatized with: 3-aminopropyl
      carbonyl
<221> NAME/KEY: SITE
<222> LOCATION: (10)
<223> OTHER INFORMATION: AMIDATION=The C-terminus is Amidated

<400> SEQUENCE: 14

Lys Trp Leu Ile Gln Leu Phe His Lys Lys
 1               5                  10

<210> SEQ ID NO 15
<211> LENGTH: 10
<212> TYPE: PRT
<213> ORGANISM: derived from human
<220> FEATURE:
<223> OTHER INFORMATION: XMP.496
<221> NAME/KEY: SITE

```
<222> LOCATION: (1)
<223> OTHER INFORMATION: Position 1 is derivatized at the alpha-amino
      with: 10- amino-decylcarbonyl
<221> NAME/KEY: SITE
<222> LOCATION: (1)..(10)
<223> OTHER INFORMATION: Positions 1-10 are D-Amino Acids
<221> NAME/KEY: SITE
<222> LOCATION: (10)
<223> OTHER INFORMATION: AMIDATION=The C-terminus is Amidated

<400> SEQUENCE: 15

Lys Trp Leu Ile Gln Leu Phe His Lys Lys
 1               5                  10

<210> SEQ ID NO 16
<211> LENGTH: 10
<212> TYPE: PRT
<213> ORGANISM: derived from human
<220> FEATURE:
<223> OTHER INFORMATION: XMP.499
<221> NAME/KEY: SITE
<222> LOCATION: (1)
<223> OTHER INFORMATION: Position 1 is derivatized at the alpha-amino
      with: 2-pyrazine carbonyl
<221> NAME/KEY: SITE
<222> LOCATION: (1)..(10)
<223> OTHER INFORMATION: Positions 1-10 are D-Amino Acids
<221> NAME/KEY: SITE
<222> LOCATION: (10)
<223> OTHER INFORMATION: AMIDATION=The C-terminus is Amidated

<400> SEQUENCE: 16

Lys Trp Leu Ile Gln Leu Phe His Lys Lys
 1               5                  10

<210> SEQ ID NO 17
<211> LENGTH: 10
<212> TYPE: PRT
<213> ORGANISM: derived from human
<220> FEATURE:
<223> OTHER INFORMATION: XMP.500
<221> NAME/KEY: SITE
<222> LOCATION: (1)
<223> OTHER INFORMATION: Position 1 is derivatized at the alpha-amino
      with: 4-imidazole carbonyl
<221> NAME/KEY: SITE
<222> LOCATION: (1)..(10)
<223> OTHER INFORMATION: Positions 1-10 are D-Amino Acids
<221> NAME/KEY: SITE
<222> LOCATION: (10)
<223> OTHER INFORMATION: AMIDATION=The C-terminus is Amidated

<400> SEQUENCE: 17

Lys Trp Leu Ile Gln Leu Phe His Lys Lys
 1               5                  10

<210> SEQ ID NO 18
<211> LENGTH: 10
<212> TYPE: PRT
<213> ORGANISM: derived from human
<220> FEATURE:
<223> OTHER INFORMATION: XMP.501
<221> NAME/KEY: SITE
<222> LOCATION: (1)
<223> OTHER INFORMATION: Position 1 is derivatized at the alpha-amino
      with: 1-(4-imidazole) methylene carbonyl
<221> NAME/KEY: SITE
<222> LOCATION: (1)..(10)
<223> OTHER INFORMATION: Positions 1-10 are D-Amino Acids
<221> NAME/KEY: SITE
<222> LOCATION: (10)
<223> OTHER INFORMATION: AMIDATION=The C-terminus is Amidated
```

```
<400> SEQUENCE: 18

Lys Trp Leu Ile Gln Leu Phe His Lys Lys
 1               5                  10

<210> SEQ ID NO 19
<211> LENGTH: 10
<212> TYPE: PRT
<213> ORGANISM: derived from human
<220> FEATURE:
<223> OTHER INFORMATION: XMP.502
<221> NAME/KEY: SITE
<222> LOCATION: (1)
<223> OTHER INFORMATION: Position 1 is derivatized at the  alpha-amino
      with:  2-imino-1- imidazolidine methylene carbonyl
<221> NAME/KEY: SITE
<222> LOCATION: (1)..(10)
<223> OTHER INFORMATION: Positions 1-10 are D-Amino Acids
<221> NAME/KEY: SITE
<222> LOCATION: (10)
<223> OTHER INFORMATION: AMIDATION=The C-terminus is Amidated

<400> SEQUENCE: 19

Lys Trp Leu Ile Gln Leu Phe His Lys Lys
 1               5                  10

<210> SEQ ID NO 20
<211> LENGTH: 10
<212> TYPE: PRT
<213> ORGANISM: derived from human
<220> FEATURE:
<223> OTHER INFORMATION: XMP.503
<221> NAME/KEY: SITE
<222> LOCATION: (1)
<223> OTHER INFORMATION: Position 1 is derivatized at the alpha-amino
      with: pyridine carbonyl
<221> NAME/KEY: SITE
<222> LOCATION: (1)..(10)
<223> OTHER INFORMATION: Positions 1-10 are D-Amino Acids
<221> NAME/KEY: SITE
<222> LOCATION: (10)
<223> OTHER INFORMATION: AMIDATION=The C-terminus is Amidated

<400> SEQUENCE: 20

Lys Trp Leu Ile Gln Leu Phe His Lys Lys
 1               5                  10

<210> SEQ ID NO 21
<211> LENGTH: 10
<212> TYPE: PRT
<213> ORGANISM: derived from human
<220> FEATURE:
<223> OTHER INFORMATION: XMP.504
<221> NAME/KEY: SITE
<222> LOCATION: (1)
<223> OTHER INFORMATION: Position 1 is derivatized at the alpha-amino
      with: 3-piperidine carbonyl
<221> NAME/KEY: SITE
<222> LOCATION: (1)..(10)
<223> OTHER INFORMATION: Positions 1-10 are D-Amino Acids
<221> NAME/KEY: SITE
<222> LOCATION: (10)
<223> OTHER INFORMATION: AMIDATION=The C-terminus is Amidated

<400> SEQUENCE: 21

Lys Trp Leu Ile Gln Leu Phe His Lys Lys
 1               5                  10

<210> SEQ ID NO 22
<211> LENGTH: 10
<212> TYPE: PRT
<213> ORGANISM: derived from human
```

```
<220> FEATURE:
<223> OTHER INFORMATION: XMP.516
<221> NAME/KEY: SITE
<222> LOCATION: (1)
<223> OTHER INFORMATION: Position 1 is derivatized at the alpha-amino
      with: acetyl
<221> NAME/KEY: SITE
<222> LOCATION: (9)
<223> OTHER INFORMATION: Position 9 is derivatized at the epsilon-amino
      with:  fluorescein
<221> NAME/KEY: SITE
<222> LOCATION: (1)..(10)
<223> OTHER INFORMATION: Positions 1-10 are D-Amino Acids
<221> NAME/KEY: SITE
<222> LOCATION: (10)
<223> OTHER INFORMATION: AMIDATION=The C-terminus is Amidated

<400> SEQUENCE: 22

Lys Trp Leu Ile Gln Leu Phe His Lys Lys
  1               5                  10

<210> SEQ ID NO 23
<211> LENGTH: 10
<212> TYPE: PRT
<213> ORGANISM: derived from human
<220> FEATURE:
<223> OTHER INFORMATION: XMP.517
<221> NAME/KEY: SITE
<222> LOCATION: (1)
<223> OTHER INFORMATION: Position 1 is derivatized at the alpha-amino
      with: acetyl
<221> NAME/KEY: SITE
<222> LOCATION: (10)
<223> OTHER INFORMATION: Position 10 is derivatized at the epsilon-amino
      with:  fluorescein
<221> NAME/KEY: SITE
<222> LOCATION: (1)..(10)
<223> OTHER INFORMATION: Positions 1-10 are D-Amino Acid
<221> NAME/KEY: SITE
<222> LOCATION: (10)
<223> OTHER INFORMATION: AMIDATION=The C-terminus is Amidated

<400> SEQUENCE: 23

Lys Trp Leu Ile Gln Leu Phe His Lys Lys
  1               5                  10

<210> SEQ ID NO 24
<211> LENGTH: 10
<212> TYPE: PRT
<213> ORGANISM: derived from human
<220> FEATURE:
<223> OTHER INFORMATION: XMP.518
<221> NAME/KEY: SITE
<222> LOCATION: (1)
<223> OTHER INFORMATION: Position 1 is derivatized at the alpha-amino
      with: acetyl
<221> NAME/KEY: SITE
<222> LOCATION: (10)
<223> OTHER INFORMATION: Position 10 is derivatized at the epsilon-amino
      with:  biotin-carbonyl
<221> NAME/KEY: SITE
<222> LOCATION: (1)..(10)
<223> OTHER INFORMATION: Positions 1-10 are D-Amino Acids
<221> NAME/KEY: SITE
<222> LOCATION: (10)
<223> OTHER INFORMATION: AMIDATION=The C-terminus is Amidated

<400> SEQUENCE: 24

Lys Trp Leu Ile Gln Leu Phe His Lys Lys
  1               5                  10

<210> SEQ ID NO 25
<211> LENGTH: 10
```

```
<212> TYPE: PRT
<213> ORGANISM: derived from human
<220> FEATURE:
<223> OTHER INFORMATION: XMP.519
<221> NAME/KEY: SITE
<222> LOCATION: (1)
<223> OTHER INFORMATION: Position 1 is derivatized at the alpha-amino
      with: biotin-carbonyl
<221> NAME/KEY: SITE
<222> LOCATION: (1)..(10)
<223> OTHER INFORMATION: Positions 1-10 are D-Amino Acids
<221> NAME/KEY: SITE
<222> LOCATION: (10)
<223> OTHER INFORMATION: AMIDATION=The C-terminus is Amidated

<400> SEQUENCE: 25

Lys Trp Leu Ile Gln Leu Phe His Lys Lys
 1               5                  10

<210> SEQ ID NO 26
<211> LENGTH: 10
<212> TYPE: PRT
<213> ORGANISM: derived from human
<220> FEATURE:
<223> OTHER INFORMATION: XMP.520
<221> NAME/KEY: SITE
<222> LOCATION: (1)
<223> OTHER INFORMATION: Position 1 is derivatized at the alpha-amino
      with: acetyl
<221> NAME/KEY: SITE
<222> LOCATION: (10)
<223> OTHER INFORMATION: Position 10 is derivatized at the carboxy
      terminus with: 2-(N-fluoroscein)diaminopropylamide
<221> NAME/KEY: SITE
<222> LOCATION: (1)..(10)
<223> OTHER INFORMATION: Position 1-10 are D-Amino Acids

<400> SEQUENCE: 26

Lys Trp Leu Ile Gln Leu Phe His Lys Lys
 1               5                  10

<210> SEQ ID NO 27
<211> LENGTH: 10
<212> TYPE: PRT
<213> ORGANISM: derived from human
<220> FEATURE:
<223> OTHER INFORMATION: XMP.521
<221> NAME/KEY: SITE
<222> LOCATION: (1)
<223> OTHER INFORMATION: Position 1 is derivatized at the alpha-amino
      with: acetyl
<221> NAME/KEY: SITE
<222> LOCATION: (9)
<223> OTHER INFORMATION: Position 9 is derivatized at the epsilon-amino
      with:  biotin-carbonyl
<221> NAME/KEY: SITE
<222> LOCATION: (1)..(10)
<223> OTHER INFORMATION: Positions 1-10 are D-Amino Acids
<221> NAME/KEY: SITE
<222> LOCATION: (10)
<223> OTHER INFORMATION: AMIDATION=The C-terminus is Amidated

<400> SEQUENCE: 27

Lys Trp Leu Ile Gln Leu Phe His Lys Lys
 1               5                  10

<210> SEQ ID NO 28
<211> LENGTH: 10
<212> TYPE: PRT
<213> ORGANISM: derived from human
<220> FEATURE:
<223> OTHER INFORMATION: XMP.522
<221> NAME/KEY: SITE
```

```
<222> LOCATION: (1)
<223> OTHER INFORMATION: Position 1 is derivatized at the alpha-amino
      with: acetyl
<221> NAME/KEY: SITE
<222> LOCATION: (9)
<223> OTHER INFORMATION: Position 9 is derivatized at the epsilon-amino
      with:  5-azido-2-nitrobenzoyl
<221> NAME/KEY: SITE
<222> LOCATION: (1)..(10)
<223> OTHER INFORMATION: Positions 1-10 are D-Amino Acids
<221> NAME/KEY: SITE
<222> LOCATION: (10)
<223> OTHER INFORMATION: AMIDATION=The C-terminus is Amidated

<400> SEQUENCE: 28

Lys Trp Leu Ile Gln Leu Phe His Lys Lys
  1               5                  10

<210> SEQ ID NO 29
<211> LENGTH: 10
<212> TYPE: PRT
<213> ORGANISM: derived from human
<220> FEATURE:
<223> OTHER INFORMATION: XMP.523
<221> NAME/KEY: SITE
<222> LOCATION: (1)
<223> OTHER INFORMATION: Position 1 is derivatized at the alpha-amino
      with: 2-(4-imidazole) acetyl
<221> NAME/KEY: SITE
<222> LOCATION: (9)
<223> OTHER INFORMATION: Position 9 is derivatized at the epsilon-amino
      with:  5-azido-2-nitrobenzoyl
<221> NAME/KEY: SITE
<222> LOCATION: (1)..(10)
<223> OTHER INFORMATION: Positions 1-10 are D-Amino Acids
<221> NAME/KEY: SITE
<222> LOCATION: (10)
<223> OTHER INFORMATION: AMIDATION=The C-terminus is Amidated

<400> SEQUENCE: 29

Lys Trp Leu Ile Gln Leu Phe His Lys Lys
  1               5                  10

<210> SEQ ID NO 30
<211> LENGTH: 10
<212> TYPE: PRT
<213> ORGANISM: derived from human
<220> FEATURE:
<223> OTHER INFORMATION: XMP.524
<221> NAME/KEY: SITE
<222> LOCATION: (1)
<223> OTHER INFORMATION: Position 1 is derivatized at the alpha-amino
      with: 4-piperidine carbonyl
<221> NAME/KEY: SITE
<222> LOCATION: (9)
<223> OTHER INFORMATION: Position 9 is derivatized at the epsilon-amino
      with:  5-azido-2-nitrobenzoyl
<221> NAME/KEY: SITE
<222> LOCATION: (1)..(10)
<223> OTHER INFORMATION: Positions 1-10 are D-Amino Acids
<221> NAME/KEY: SITE
<222> LOCATION: (10)
<223> OTHER INFORMATION: AMIDATION=The C-terminus is Amidated

<400> SEQUENCE: 30

Lys Trp Leu Ile Gln Leu Phe His Lys Lys
  1               5                  10

<210> SEQ ID NO 31
<211> LENGTH: 10
<212> TYPE: PRT
<213> ORGANISM: derived from human
<220> FEATURE:
```

<223> OTHER INFORMATION: XMP.525
<221> NAME/KEY: SITE
<222> LOCATION: (1)
<223> OTHER INFORMATION: Position 1 is derivatized at the alpha-amino
      with: 2-(2-imino-1-imidazolidine) acetyl
<221> NAME/KEY: SITE
<222> LOCATION: (9)
<223> OTHER INFORMATION: Position 9 is derivatized at the epsilon-amino
      with:  5-azido-2-nitrobenzoyl
<221> NAME/KEY: SITE
<222> LOCATION: (1)..(10)
<223> OTHER INFORMATION: Positions 1-10 are D-Amino Acids
<221> NAME/KEY: SITE
<222> LOCATION: (10)
<223> OTHER INFORMATION: AMIDATION=The C-terminus is Amidated

<400> SEQUENCE: 31

Lys Trp Leu Ile Gln Leu Phe His Lys Lys
 1               5                  10

<210> SEQ ID NO 32
<211> LENGTH: 10
<212> TYPE: PRT
<213> ORGANISM: derived from human
<220> FEATURE:
<223> OTHER INFORMATION: XMP.526
<221> NAME/KEY: SITE
<222> LOCATION: (1)
<223> OTHER INFORMATION: Position 1 is derivatized at the alpha-amino
      with: acetyl
<221> NAME/KEY: SITE
<222> LOCATION: (9)
<223> OTHER INFORMATION: Position 9 is derivatized at the epsilon-amino
      with:  N-hydroxysuccinimidyl-4-azidosalicylyl
<221> NAME/KEY: SITE
<222> LOCATION: (1)..(10)
<223> OTHER INFORMATION: Positions 1-10 are D-Amino Acids
<221> NAME/KEY: SITE
<222> LOCATION: (10)
<223> OTHER INFORMATION: AMIDATION=The C-terminus is Amidated

<400> SEQUENCE: 32

Lys Trp Leu Ile Gln Leu Phe His Lys Lys
 1               5                  10

<210> SEQ ID NO 33
<211> LENGTH: 10
<212> TYPE: PRT
<213> ORGANISM: derived from human
<220> FEATURE:
<223> OTHER INFORMATION: XMP.527
<221> NAME/KEY: SITE
<222> LOCATION: (1)
<223> OTHER INFORMATION: Position 1 is derivatized at the alpha-amino
      with: acetyl
<221> NAME/KEY: SITE
<222> LOCATION: (9)
<223> OTHER INFORMATION: Position 9 is derivatized at the epsilon-amino
      with:  N-hydroxysulphosuccinimidyl-4-azidobenzoyl
<221> NAME/KEY: SITE
<222> LOCATION: (1)..(10)
<223> OTHER INFORMATION: Positions 1-10 are D-Amino Acids
<221> NAME/KEY: SITE
<222> LOCATION: (10)
<223> OTHER INFORMATION: AMIDATION=The C-terminus is Amidated

<400> SEQUENCE: 33

Lys Trp Leu Ile Gln Leu Phe His Lys Lys
 1               5                  10

<210> SEQ ID NO 34
<211> LENGTH: 11
<212> TYPE: PRT

```
<213> ORGANISM: derived from human
<220> FEATURE:
<223> OTHER INFORMATION: XMP.532
<221> NAME/KEY: SITE
<222> LOCATION: (1)..(11)
<223> OTHER INFORMATION: Positions 1-11 are L-amino acids
<221> NAME/KEY: SITE
<222> LOCATION: (11)
<223> OTHER INFORMATION: AMIDATION=The C-terminus is Amidated

<400> SEQUENCE: 34

Lys Val Trp Leu Ile Gln Leu Phe His Lys Lys
  1               5                  10

<210> SEQ ID NO 35
<211> LENGTH: 10
<212> TYPE: PRT
<213> ORGANISM: derived from human
<220> FEATURE:
<223> OTHER INFORMATION: XMP.533
<221> NAME/KEY: SITE
<222> LOCATION: (1)
<223> OTHER INFORMATION: Position 1 is derivatized at the alpha-amino
      with: 2- quinoxal carbonyl
<221> NAME/KEY: SITE
<222> LOCATION: (1)..(10)
<223> OTHER INFORMATION: Positions 1-10 are D-Amino Acids
<221> NAME/KEY: SITE
<222> LOCATION: (10)
<223> OTHER INFORMATION: AMIDATION=The C-terminus is Amidated

<400> SEQUENCE: 35

Lys Trp Leu Ile Gln Leu Phe His Lys Lys
  1               5                  10

<210> SEQ ID NO 36
<211> LENGTH: 10
<212> TYPE: PRT
<213> ORGANISM: derived from human
<220> FEATURE:
<223> OTHER INFORMATION: XMP.534
<221> NAME/KEY: SITE
<222> LOCATION: (1)
<223> OTHER INFORMATION: Position 1 is derivatized at the alpha-amino
      with: biphenylene-carbonyl
<221> NAME/KEY: SITE
<222> LOCATION: (1)..(10)
<223> OTHER INFORMATION: Positions 1-10 are D-Amino Acids
<221> NAME/KEY: SITE
<222> LOCATION: (10)
<223> OTHER INFORMATION: AMIDATION=The C-terminus is Amidated

<400> SEQUENCE: 36

Lys Trp Leu Ile Gln Leu Phe His Lys Lys
  1               5                  10

<210> SEQ ID NO 37
<211> LENGTH: 10
<212> TYPE: PRT
<213> ORGANISM: derived from human
<220> FEATURE:
<223> OTHER INFORMATION: XMP.535
<221> NAME/KEY: SITE
<222> LOCATION: (1)
<223> OTHER INFORMATION: Position 1 is derivatized at the alpha-amino
      with: anthraquinone carbonyl
<221> NAME/KEY: SITE
<222> LOCATION: (1)..(10)
<223> OTHER INFORMATION: Positions 1-10 are D-Amino Acids
<221> NAME/KEY: SITE
<222> LOCATION: (10)
<223> OTHER INFORMATION: AMIDATION=The C-terminus is Amidated
```

```
<400> SEQUENCE: 37

Lys Trp Leu Ile Gln Leu Phe His Lys Lys
 1               5                  10

<210> SEQ ID NO 38
<211> LENGTH: 10
<212> TYPE: PRT
<213> ORGANISM: derived from human
<220> FEATURE:
<223> OTHER INFORMATION: XMP.536
<221> NAME/KEY: SITE
<222> LOCATION: (1)
<223> OTHER INFORMATION: Position 1 is derivatized at the alpha-amino
      with: benzofuran-carbonyl
<221> NAME/KEY: SITE
<222> LOCATION: (1)..(10)
<223> OTHER INFORMATION: Positions 1-10 are D-Amino Acids
<221> NAME/KEY: SITE
<222> LOCATION: ()
<223> OTHER INFORMATION: AMIDATION=The C-terminus is Amidated

<400> SEQUENCE: 38

Lys Trp Leu Ile Gln Leu Phe His Lys Lys
 1               5                  10

<210> SEQ ID NO 39
<211> LENGTH: 10
<212> TYPE: PRT
<213> ORGANISM: derived from human
<220> FEATURE:
<223> OTHER INFORMATION: XMP.545
<221> NAME/KEY: SITE
<222> LOCATION: (1)
<223> OTHER INFORMATION: Position 1 is derivatized at the alpha-amino
      with: indole-carbonyl
<221> NAME/KEY: SITE
<222> LOCATION: (1)..(10)
<223> OTHER INFORMATION: Positions 1-10 are D-Amino Acids
<221> NAME/KEY: SITE
<222> LOCATION: (10)
<223> OTHER INFORMATION: AMIDATION=The C-terminus is Amidated

<400> SEQUENCE: 39

Lys Trp Leu Ile Gln Leu Phe His Lys Lys
 1               5                  10

<210> SEQ ID NO 40
<211> LENGTH: 10
<212> TYPE: PRT
<213> ORGANISM: derived from human
<220> FEATURE:
<223> OTHER INFORMATION: XMP.546
<221> NAME/KEY: SITE
<222> LOCATION: (1)
<223> OTHER INFORMATION: Position 1 is derivatized at the alpha-amino
      with: 1-isoquinoline-carbonyl
<221> NAME/KEY: SITE
<222> LOCATION: (1)..(10)
<223> OTHER INFORMATION: Positions 1-10 are D-Amino Acids
<221> NAME/KEY: SITE
<222> LOCATION: (10)
<223> OTHER INFORMATION: AMIDATION=The C-terminus is Amidated

<400> SEQUENCE: 40

Lys Trp Leu Ile Gln Leu Phe His Lys Lys
 1               5                  10

<210> SEQ ID NO 41
<211> LENGTH: 10
<212> TYPE: PRT
<213> ORGANISM: derived from human
```

```
<220> FEATURE:
<223> OTHER INFORMATION: XMP.560
<221> NAME/KEY: SITE
<222> LOCATION: (1)
<223> OTHER INFORMATION: Position 1 is derivatized at the alpha-amino
      with: salicylic-carbonyl
<221> NAME/KEY: SITE
<222> LOCATION: (1)..(10)
<223> OTHER INFORMATION: Positions 1-10 are D-Amino Acids
<221> NAME/KEY: SITE
<222> LOCATION: (10)
<223> OTHER INFORMATION: AMIDATION=The C-terminus is Amidated

<400> SEQUENCE: 41

Lys Trp Leu Ile Gln Leu Phe His Lys Lys
  1               5                  10

<210> SEQ ID NO 42
<211> LENGTH: 12
<212> TYPE: PRT
<213> ORGANISM: derived from human
<220> FEATURE:
<223> OTHER INFORMATION: XMP.565
<221> NAME/KEY: SITE
<222> LOCATION: (9)
<223> OTHER INFORMATION: Position 9 Xaa=amino isobutyric acid
<221> NAME/KEY: SITE
<222> LOCATION: (1)..(12)
<223> OTHER INFORMATION: Positions 1-12 are L-amino acids
<221> NAME/KEY: SITE
<222> LOCATION: (12)
<223> OTHER INFORMATION: AMIDATION=The C-terminus is Amidated

<400> SEQUENCE: 42

Lys Val Gly Trp Leu Ile Gln Leu Xaa His Lys Lys
  1               5                  10

<210> SEQ ID NO 43
<211> LENGTH: 10
<212> TYPE: PRT
<213> ORGANISM: derived from human
<220> FEATURE:
<223> OTHER INFORMATION: XMP.596
<221> NAME/KEY: SITE
<222> LOCATION: (1)
<223> OTHER INFORMATION: Position 1 is derivatized at the alpha-amino
      with: quinaldic-carbonyl
<221> NAME/KEY: SITE
<222> LOCATION: (1)..(10)
<223> OTHER INFORMATION: Positions 1-10 are D-Amino Acids
<221> NAME/KEY: SITE
<222> LOCATION: (10)
<223> OTHER INFORMATION: AMIDATION=The C-terminus is Amidated

<400> SEQUENCE: 43

Lys Trp Leu Ile Gln Leu Phe His Lys Lys
  1               5                  10

<210> SEQ ID NO 44
<211> LENGTH: 9
<212> TYPE: PRT
<213> ORGANISM: derived from human
<220> FEATURE:
<223> OTHER INFORMATION: XMP.599
<221> NAME/KEY: SITE
<222> LOCATION: (1)
<223> OTHER INFORMATION: Position 1 is derivatized at the alpha-amino
      with: 2-(amino-3,5,6-trichloropyridine) carbonyl
<221> NAME/KEY: SITE
<222> LOCATION: (1)..(9)
<223> OTHER INFORMATION: Positions 1-9 are D-Amino Acids
<221> NAME/KEY: SITE
<222> LOCATION: (9)
```

<223> OTHER INFORMATION: AMIDATION=The C=terminus is Amidated

<400> SEQUENCE: 44

Lys Trp Leu Gln Leu Phe His Lys Lys
 1               5

<210> SEQ ID NO 45
<211> LENGTH: 9
<212> TYPE: PRT
<213> ORGANISM: derived from human
<220> FEATURE:
<223> OTHER INFORMATION: XMP.600
<221> NAME/KEY: SITE
<222> LOCATION: (1)
<223> OTHER INFORMATION: Position 1 is derivatized at the alpha-amino
      with: 3-chloro-2-nitrobenzoyl
<221> NAME/KEY: SITE
<222> LOCATION: (1)..(9)
<223> OTHER INFORMATION: Positions 1-9 are D-Amino Acids
<221> NAME/KEY: SITE
<222> LOCATION: (9)
<223> OTHER INFORMATION: AMIDATION=The C-terminus is Amidated

<400> SEQUENCE: 45

Lys Trp Leu Gln Leu Phe His Lys Lys
 1               5

<210> SEQ ID NO 46
<211> LENGTH: 9
<212> TYPE: PRT
<213> ORGANISM: derived from human
<220> FEATURE:
<223> OTHER INFORMATION: XMP.601
<221> NAME/KEY: SITE
<222> LOCATION: (1)
<223> OTHER INFORMATION: Position 1 is derivatized at the alpha-amino
      with: 3(2-chloro-6-fluorophenyl)-5-methylisoxazole-4-ca
      rbonyl
<221> NAME/KEY: SITE
<222> LOCATION: (1)..(9)
<223> OTHER INFORMATION: Positions 1-9 are D-Amino Acids
<221> NAME/KEY: SITE
<222> LOCATION: (9)
<223> OTHER INFORMATION: AMIDATION=The C-terminus is Amidated

<400> SEQUENCE: 46

Lys Trp Leu Gln Leu Phe His Lys Lys
 1               5

<210> SEQ ID NO 47
<211> LENGTH: 9
<212> TYPE: PRT
<213> ORGANISM: derived from human
<220> FEATURE:
<223> OTHER INFORMATION: XMP.606
<221> NAME/KEY: SITE
<222> LOCATION: (1)
<223> OTHER INFORMATION: Position 1 is derivatized at the alpha-amino
      with: chlorogenic 1-[3-(3,4-Dihydroxycinnamoyl)-1,3,4,
      5-tetrahydroxy cyclohexane]
<221> NAME/KEY: SITE
<222> LOCATION: (1)..(9)
<223> OTHER INFORMATION: Positions 1-9 are D-Amino Acids
<221> NAME/KEY: SITE
<222> LOCATION: (9)
<223> OTHER INFORMATION: AMIDATION=the C-terminus is Amidated

<400> SEQUENCE: 47

Lys Trp Leu Gln Leu Phe His Lys Lys
 1               5

```
<210> SEQ ID NO 48
<211> LENGTH: 10
<212> TYPE: PRT
<213> ORGANISM: derived from human
<220> FEATURE:
<223> OTHER INFORMATION: XMP.618
<221> NAME/KEY: SITE
<222> LOCATION: (1)
<223> OTHER INFORMATION: Position 1 is derivatized at the alpha-amino
      with: 2-nitro-3-chloro-benzoyl
<221> NAME/KEY: SITE
<222> LOCATION: (1)..(10)
<223> OTHER INFORMATION: Positions 1-10 are D-Amino Acids
<221> NAME/KEY: SITE
<222> LOCATION: (10)
<223> OTHER INFORMATION: AMIDATION=The C-terminus is Amidated

<400> SEQUENCE: 48

Lys Trp Leu Ile Gln Leu Phe His Lys Lys
 1               5                  10

<210> SEQ ID NO 49
<211> LENGTH: 10
<212> TYPE: PRT
<213> ORGANISM: derived from human
<220> FEATURE:
<223> OTHER INFORMATION: XMP.620
<221> NAME/KEY: SITE
<222> LOCATION: (1)..(2)
<223> OTHER INFORMATION: Positions 1-2 are D-amino acids
<221> NAME/KEY: SITE
<222> LOCATION: (9)..(10)
<223> OTHER INFORMATION: Positions 9-10 are D-amino acids
<221> NAME/KEY: SITE
<222> LOCATION: (3)..(8)
<223> OTHER INFORMATION: Positions 3-8 are L-amino acids
<221> NAME/KEY: SITE
<222> LOCATION: (10)
<223> OTHER INFORMATION: AMIDATION=The C-terminus is Amidated

<400> SEQUENCE: 49

Lys Trp Leu Ile Gln Leu Phe His Lys Lys
 1               5                  10

<210> SEQ ID NO 50
<211> LENGTH: 10
<212> TYPE: PRT
<213> ORGANISM: derived from human
<220> FEATURE:
<223> OTHER INFORMATION: XMP.642
<221> NAME/KEY: SITE
<222> LOCATION: (1)..(10)
<223> OTHER INFORMATION: Positions 1-10 are L-amino acids
<221> NAME/KEY: SITE
<222> LOCATION: (10)
<223> OTHER INFORMATION: AMIDATION=The C-terminus is Amidated

<400> SEQUENCE: 50

Lys Val Leu Ile Gln Leu Phe His Lys Lys
 1               5                  10

<210> SEQ ID NO 51
<211> LENGTH: 12
<212> TYPE: PRT
<213> ORGANISM: derived from human
<220> FEATURE:
<223> OTHER INFORMATION: XMP.653
<221> NAME/KEY: SITE
<222> LOCATION: (1)..(12)
<223> OTHER INFORMATION: Positions 1-12 are L-amino acids
<221> NAME/KEY: SITE
<222> LOCATION: (12)
<223> OTHER INFORMATION: AMIDATION=The C-terminus is Amidated
```

```
<400> SEQUENCE: 51

Lys Val Tyr Trp Leu Ile Gln Leu Phe His Lys Lys
 1               5                  10

<210> SEQ ID NO 52
<211> LENGTH: 10
<212> TYPE: PRT
<213> ORGANISM: derived from human
<220> FEATURE:
<223> OTHER INFORMATION: XMP.678
<221> NAME/KEY: SITE
<222> LOCATION: (1)..(10)
<223> OTHER INFORMATION: Positions 1-10 are L-amino acids
<221> NAME/KEY: SITE
<222> LOCATION: (10)
<223> OTHER INFORMATION: AMIDATION=The C-terminus is Amidated

<400> SEQUENCE: 52

Lys Val Leu Val Gln Leu Phe His Lys Lys
 1               5                  10

<210> SEQ ID NO 53
<211> LENGTH: 1813
<212> TYPE: DNA
<213> ORGANISM: human
<220> FEATURE:
<221> NAME/KEY: CDS
<222> LOCATION: (31)..(1491)
<221> NAME/KEY: mat_peptide
<222> LOCATION: (124)..(1491)

<400> SEQUENCE: 53
```

| | | |
|---|---|---|
| caggccttga ggttttggca gctctggagg atg aga gag aac atg gcc agg ggc<br>                                                             Met Arg Glu Asn Met Ala Arg Gly<br>                                                              -30                   -25 | 54 |

```
cct tgc aac gcg ccg aga tgg gtg tcc ctg atg gtg ctc gtc gcc ata    102
Pro Cys Asn Ala Pro Arg Trp Val Ser Leu Met Val Leu Val Ala Ile
        -20                 -15                 -10 ggc acc gcc gtg aca gcg gcc gtc aac cct ggc gtc gtg gtc agg atc    150
Gly Thr Ala Val Thr Ala Ala Val Asn Pro Gly Val Val Val Arg Ile
         -5                  -1   1                   5 tcc cag aag ggc ctg gac tac gcc agc cag cag ggg acg gcc gct ctg    198
Ser Gln Lys Gly Leu Asp Tyr Ala Ser Gln Gln Gly Thr Ala Ala Leu
 10                  15                  20                  25 cag aag gag ctg aag agg atc aag att cct gac tac tca gac agc ttt    246
Gln Lys Glu Leu Lys Arg Ile Lys Ile Pro Asp Tyr Ser Asp Ser Phe
                 30                  35                  40 aag atc aag cat ctt ggg aag ggg cat tat agc ttc tac agc atg gac    294
Lys Ile Lys His Leu Gly Lys Gly His Tyr Ser Phe Tyr Ser Met Asp
             45                  50                  55 atc cgt gaa ttc cag ctt ccc agt tcc cag ata agc atg gtg ccc aat    342
Ile Arg Glu Phe Gln Leu Pro Ser Ser Gln Ile Ser Met Val Pro Asn
         60                  65                  70 gtg ggc ctt aag ttc tcc atc agc aac gcc aat atc aag atc agc ggg    390
Val Gly Leu Lys Phe Ser Ile Ser Asn Ala Asn Ile Lys Ile Ser Gly
     75                  80                  85 aaa tgg aag gca caa aag aga ttc tta aaa atg agc ggc aat ttt gac    438
Lys Trp Lys Ala Gln Lys Arg Phe Leu Lys Met Ser Gly Asn Phe Asp
 90                  95                 100                 105 ctg agc ata gaa ggc atg tcc att tcg gct gat ctg aag ctg ggc agt    486
Leu Ser Ile Glu Gly Met Ser Ile Ser Ala Asp Leu Lys Leu Gly Ser
                110                 115                 120 aac ccc acg tca ggc aag ccc acc atc acc tgc tcc agc tgc agc agc    534
```

```
Asn Pro Thr Ser Gly Lys Pro Thr Ile Thr Cys Ser Ser Cys Ser Ser
        125                 130                 135 cac atc aac agt gtc cac gtg cac atc tca aag agc aaa gtc ggg tgg        582
His Ile Asn Ser Val His Val His Ile Ser Lys Ser Lys Val Gly Trp
        140                 145                 150 ctg atc caa ctc ttc cac aaa aaa att gag tct gcg ctt cga aac aag        630
Leu Ile Gln Leu Phe His Lys Lys Ile Glu Ser Ala Leu Arg Asn Lys
        155                 160                 165 atg aac agc cag gtc tgc gag aaa gtg acc aat tct gta tcc tcc aag        678
Met Asn Ser Gln Val Cys Glu Lys Val Thr Asn Ser Val Ser Ser Lys
170                 175                 180                 185 ctg caa cct tat ttc cag act ctg cca gta atg acc aaa ata gat tct        726
Leu Gln Pro Tyr Phe Gln Thr Leu Pro Val Met Thr Lys Ile Asp Ser
                190                 195                 200 gtg gct gga atc aac tat ggt ctg gtg gca cct cca gca acc acg gct        774
Val Ala Gly Ile Asn Tyr Gly Leu Val Ala Pro Pro Ala Thr Thr Ala
                205                 210                 215 gag acc ctg gat gta cag atg aag ggg gag ttt tac agt gag aac cac        822
Glu Thr Leu Asp Val Gln Met Lys Gly Glu Phe Tyr Ser Glu Asn His
                220                 225                 230 cac aat cca cct ccc ttt gct cca cca gtg atg gag ttt ccc gct gcc        870
His Asn Pro Pro Pro Phe Ala Pro Pro Val Met Glu Phe Pro Ala Ala
        235                 240                 245 cat gac cgc atg gta tac ctg ggc ctc tca gac tac ttc ttc aac aca        918
His Asp Arg Met Val Tyr Leu Gly Leu Ser Asp Tyr Phe Phe Asn Thr
250                 255                 260                 265 gcc ggg ctt gta tac caa gag gct ggg gtc ttg aag atg acc ctt aga        966
Ala Gly Leu Val Tyr Gln Glu Ala Gly Val Leu Lys Met Thr Leu Arg
                270                 275                 280 gat gac atg att cca aag gag tcc aaa ttt cga ctc aca acc aag ttc       1014
Asp Asp Met Ile Pro Lys Glu Ser Lys Phe Arg Leu Thr Thr Lys Phe
                285                 290                 295 ttt gga acc ttc cta cct gag gtg gcc aag aag ttt ccc aac atg aag       1062
Phe Gly Thr Phe Leu Pro Glu Val Ala Lys Lys Phe Pro Asn Met Lys
                300                 305                 310 ata cag atc cat gtc tca gcc tcc acc ccg cca cac ctg tct gtg cag       1110
Ile Gln Ile His Val Ser Ala Ser Thr Pro Pro His Leu Ser Val Gln
        315                 320                 325 ccc acc ggc ctt acc ttc tac cct gcc gtg gat gtc cag gcc ttt gcc       1158
Pro Thr Gly Leu Thr Phe Tyr Pro Ala Val Asp Val Gln Ala Phe Ala
330                 335                 340                 345 gtc ctc ccc aac tcc tcc ctg gct tcc ctc ttc ctg att ggc atg cac       1206
Val Leu Pro Asn Ser Ser Leu Ala Ser Leu Phe Leu Ile Gly Met His
                350                 355                 360 aca act ggt tcc atg gag gtc agc gcc gag tcc aac agg ctt gtt gga       1254
Thr Thr Gly Ser Met Glu Val Ser Ala Glu Ser Asn Arg Leu Val Gly
                365                 370                 375 gag ctc aag ctg gat agg ctg ctc ctg gaa ctg aag cac tca aat att       1302
Glu Leu Lys Leu Asp Arg Leu Leu Leu Glu Leu Lys His Ser Asn Ile
                380                 385                 390 ggc ccc ttc ccg gtt gaa ttg ctg cag gat atc atg aac tac att gta       1350
Gly Pro Phe Pro Val Glu Leu Leu Gln Asp Ile Met Asn Tyr Ile Val
        395                 400                 405 ccc att ctt gtg ctg ccc agg gtt aac gag aaa cta cag aaa ggc ttc       1398
Pro Ile Leu Val Leu Pro Arg Val Asn Glu Lys Leu Gln Lys Gly Phe
410                 415                 420                 425 cct ctc ccg acg ccg gcc aga gtc cag ctc tac aac gta gtg ctt cag       1446
Pro Leu Pro Thr Pro Ala Arg Val Gln Leu Tyr Asn Val Val Leu Gln
                430                 435                 440
```

```
cct cac cag aac ttc ctg ctg ttc ggt gca gac gtt gtc tat aaa                1491
Pro His Gln Asn Phe Leu Leu Phe Gly Ala Asp Val Val Tyr Lys
            445                 450                 455 tgaaggcacc agggtgccg gggctgtca ccgcacctg ttcctgatgg gctgtggggc              1551
accggctgcc tttccccagg gaatcctctc cagatcttaa ccaagagccc cttgcaaact           1611
tcttcgactc agattcagaa atgatctaaa cacgaggaaa cattattcat tggaaaagtg           1671
catggtgtgt attttaggga ttatgagctt ctttcaaggg ctaaggctgc agagatattt          1731
cctccaggaa tcgtgtttca attgtaacca agaaatttcc atttgtgctt catgaaaaaa          1791
aacttctggt tttttcatg tg                                                     1813
```

<210> SEQ ID NO 54
<211> LENGTH: 487
<212> TYPE: PRT
<213> ORGANISM: human

<400> SEQUENCE: 54

```
Met Arg Glu Asn Met Ala Arg Gly Pro Cys Asn Ala Pro Arg Trp Val
        -30                 -25                 -20

Ser Leu Met Val Leu Val Ala Ile Gly Thr Ala Val Thr Ala Ala Val
-15                 -10                  -5                 -1   1

Asn Pro Gly Val Val Arg Ile Ser Gln Lys Gly Leu Asp Tyr Ala
                 5                  10                  15

Ser Gln Gln Gly Thr Ala Ala Leu Gln Lys Glu Leu Lys Arg Ile Lys
            20                  25                  30

Ile Pro Asp Tyr Ser Asp Ser Phe Lys Ile Lys His Leu Gly Lys Gly
        35                  40                  45

His Tyr Ser Phe Tyr Ser Met Asp Ile Arg Glu Phe Gln Leu Pro Ser
 50                  55                  60                  65

Ser Gln Ile Ser Met Val Pro Asn Val Gly Leu Lys Phe Ser Ile Ser
                 70                  75                  80

Asn Ala Asn Ile Lys Ile Ser Gly Lys Trp Lys Ala Gln Lys Arg Phe
            85                  90                  95

Leu Lys Met Ser Gly Asn Phe Asp Leu Ser Ile Glu Gly Met Ser Ile
        100                 105                 110

Ser Ala Asp Leu Lys Leu Gly Ser Asn Pro Thr Ser Gly Lys Pro Thr
    115                 120                 125

Ile Thr Cys Ser Ser Cys Ser Ser His Ile Asn Ser Val His Val His
130                 135                 140                 145

Ile Ser Lys Ser Lys Val Gly Trp Leu Ile Gln Leu Phe His Lys Lys
                150                 155                 160

Ile Glu Ser Ala Leu Arg Asn Lys Met Asn Ser Gln Val Cys Glu Lys
            165                 170                 175

Val Thr Asn Ser Val Ser Ser Lys Leu Gln Pro Tyr Phe Gln Thr Leu
        180                 185                 190

Pro Val Met Thr Lys Ile Asp Ser Val Ala Gly Ile Asn Tyr Gly Leu
    195                 200                 205

Val Ala Pro Pro Ala Thr Thr Ala Glu Thr Leu Asp Val Gln Met Lys
210                 215                 220                 225

Gly Glu Phe Tyr Ser Glu Asn His His Asn Pro Pro Phe Ala Pro
                230                 235                 240

Pro Val Met Glu Phe Pro Ala Ala His Asp Arg Met Val Tyr Leu Gly
            245                 250                 255

Leu Ser Asp Tyr Phe Phe Asn Thr Ala Gly Leu Val Tyr Gln Glu Ala
```

```
                260                 265                 270
Gly Val Leu Lys Met Thr Leu Arg Asp Asp Met Ile Pro Lys Glu Ser
            275                 280                 285

Lys Phe Arg Leu Thr Thr Lys Phe Phe Gly Thr Phe Leu Pro Glu Val
290                 295                 300                 305

Ala Lys Lys Phe Pro Asn Met Lys Ile Gln Ile His Val Ser Ala Ser
                310                 315                 320

Thr Pro Pro His Leu Ser Val Gln Pro Thr Gly Leu Thr Phe Tyr Pro
            325                 330                 335

Ala Val Asp Val Gln Ala Phe Ala Val Leu Pro Asn Ser Ser Leu Ala
            340                 345                 350

Ser Leu Phe Leu Ile Gly Met His Thr Thr Gly Ser Met Glu Val Ser
            355                 360                 365

Ala Glu Ser Asn Arg Leu Val Gly Glu Leu Lys Leu Asp Arg Leu Leu
370                 375                 380                 385

Leu Glu Leu Lys His Ser Asn Ile Gly Pro Phe Pro Val Glu Leu Leu
                390                 395                 400

Gln Asp Ile Met Asn Tyr Ile Val Pro Ile Leu Val Leu Pro Arg Val
            405                 410                 415

Asn Glu Lys Leu Gln Lys Gly Phe Pro Leu Pro Thr Pro Ala Arg Val
            420                 425                 430

Gln Leu Tyr Asn Val Val Leu Gln Pro His Gly Asn Phe Leu Leu Phe
            435                 440                 445

Gly Ala Asp Val Val Tyr Lys
450                 455

<210> SEQ ID NO 55
<211> LENGTH: 4
<212> TYPE: PRT
<213> ORGANISM: Homo sapiens

<400> SEQUENCE: 55

Leu Ile Gln Leu
  1

<210> SEQ ID NO 56
<211> LENGTH: 4
<212> TYPE: PRT
<213> ORGANISM: Homo sapiens

<400> SEQUENCE: 56

Ile Gln Leu Phe
  1

<210> SEQ ID NO 57
<211> LENGTH: 5
<212> TYPE: PRT
<213> ORGANISM: Homo sapiens

<400> SEQUENCE: 57

Trp Leu Ile Gln Leu
  1               5

<210> SEQ ID NO 58
<211> LENGTH: 5
<212> TYPE: PRT
<213> ORGANISM: Homo sapiens

<400> SEQUENCE: 58
```

```
Leu Ile Gln Leu Phe
 1               5

<210> SEQ ID NO 59
<211> LENGTH: 6
<212> TYPE: PRT
<213> ORGANISM: Homo sapiens

<400> SEQUENCE: 59

Trp Leu Ile Gln Leu Phe
 1               5

<210> SEQ ID NO 60
<211> LENGTH: 10
<212> TYPE: PRT
<213> ORGANISM: Homo sapiens
<220> FEATURE:
<223> OTHER INFORMATION: Any one or all of amino acids 1-2 and 7-10 can
      either be present or absent, and any one or both
      of amino acids 9 and 10 can be lysine.

<400> SEQUENCE: 60

Xaa Xaa Leu Ile Gln Leu Xaa Xaa Xaa Xaa
 1               5                  10

<210> SEQ ID NO 61
<211> LENGTH: 11
<212> TYPE: PRT
<213> ORGANISM: Homo sapiens
<220> FEATURE:
<223> OTHER INFORMATION: Any one or all of amino acids 1-3 and 8-11 can
      either be present or absent, and any one of amino
      acids 9 and 10 can be lysine, and if amino acid 10
      is lysine then amino acid 11 can be lysine.

<400> SEQUENCE: 61

Xaa Xaa Xaa Ile Gln Leu Phe Xaa Xaa Xaa Xaa
 1               5                  10
```

DERIVATIVE COMPOUNDS DERIVED FROM OR BASED ON BACTERICIDAL/PERMEABILITY-INCREASING PROTEIN

FIELD OF THE INVENTION

The present invention relates generally to derivatized compounds that are peptide-based constructs derived from or based on Domain III (amino acids 142–169) of bactericidal/permeability-increasing protein (BPI) and therapeutic uses of such compounds.

BACKGROUND OF THE INVENTION

Bactericidal/permeability-increasing protein (BPI) is a protein isolated from the granules of mammalian polymorphonuclear leukocytes (PMNs or neutrophils), which are blood cells essential in the defense against invading microorganisms. Human BPI protein has been isolated from PMNs by acid extraction combined with either ion exchange chromatography (Elsbach, 1979, *J. Biol. Chem.* 254: 11000) or *E. coli* affinity chromatography (Weiss, 1987, et al., *Blood* 69: 652). BPI obtained in such a manner is referred to herein as natural BPI and has been shown to have bactericidal activity against gram-negative bacteria. The molecular weight of human BPI is approximately 55,000 daltons (55 kD). The amino acid sequence of the entire human BPI protein and the nucleic acid sequence of DNA encoding the protein have been reported in FIG. 1 of Gray, 1989, et al., *J. Biol. Chem.* 264: 9505. The Gray et al. DNA and amino acid sequences are set out in SEQ ID NOS: 53 and 54 hereto.

BPI is a strongly cationic protein. The N-terminal half of BPI accounts for the high net positive charge; the C-terminal half of the molecule has a net charge of −3. (Elsbach and Weiss, 1981, supra.) A proteolytic N-terminal fragment of BPI having a molecular weight of about 25 kD has an amphipathic character, containing alternating hydrophobic and hydrophilic regions. This N-terminal fragment of human BPI possesses the anti-bacterial efficacy of the naturally-derived 55 kD human BPI holoprotein. (Ooi et al., 1987, *J. Bio. Chem.* 262: 14891–14894). In contrast to the N-terminal portion, the C-terminal region of the isolated human BPI protein displays only slightly detectable anti-bacterial activity against gram-negative organisms and some endotoxin neutralizing activity. (Ooi et al., 1991, *J. Exp. Med.* 174: 649). An N-terminal BPI fragment of approximately 23 kD, referred to as "rBPI$_{23}$," has been produced by recombinant means and also retains anti-bacterial, including anti-endotoxin activity against gram-negative organisms (Gazzano-Santoro et al., 1992, *Infect. Immun.* 60: 4754–4761). In that publication, an expression vector was used as a source of DNA encoding a recombinant expression product (rBPI$_{23}$). The vector was constructed to encode the 31-residue signal sequence and the first 199 amino acids of the N-terminus of the mature human BPI, as set out in SEQ ID NOS: 53 and 54 taken from Gray et al., supra, except that valine at position 151 is specified by GTG rather than GTC and residue 185 is glutamic acid (specified by GAG) rather than lysine (specified by AAG). Recombinant holoprotein, also referred to as rBPI, has also been produced having the sequence set out in SEQ ID NOS: 53 and 54 taken from Gray et al., supra, with the exceptions noted for rBPI$_{23}$. An N-terminal fragment analog designated rBPI$_{21}$ or rBPI$_{21}$Δcys has been described in co-owned, co-pending U.S. Pat. No. 5,420,019. This analog comprises the first 193 amino acids of BPI holoprotein as set out in SEQ ID NOS: 53 and 54 but wherein the cysteine at residue number 132 is substituted with alanine, and with the exceptions noted for rBPI$_{23}$.

The bactericidal effect of BPI has been reported to be highly specific to gram-negative species, e.g., in Elsbach and Weiss, 1992, Inflammation: *Basic Principles and Clinical Correlates,* eds. Gallin et al., Chapter 30, Raven Press, Ltd. BPI is commonly thought to be non-toxic for other microorganisms, including yeast, and for higher eukaryotic cells. Elsbach and Weiss, 1992, supra, reported that BPI exhibits anti-bacterial activity towards a broad range of gram-negative bacteria at concentrations as low as $10^{-8}$ to $10^{-9}$ M, but that 100- to 1,000-fold higher concentrations of BPI were non-toxic to all of the gram-positive bacterial species, yeasts, and higher eukaryotic cells tested at that time. It was also reported that BPI at a concentration of $10^6$ M or 160 μg/ml had no toxic effect, when tested at a pH of either 7.0 or 5.5, on the gram-positive organisms *Staphylococcus aureus* (four strains), *Staphylococcus epidermidis, Streptococcus faecalis, Bacillus subtilis, Micrococcus lysodeikticus,* and *Listeria monocytogenes.* BPI at $10^{-6}$ M reportedly had no toxic effect on the fungi *Candida albicans* and *Candida parapsilosis* at pH 7.0 or 5.5, and was non-toxic to higher eukaryotic cells such as human, rabbit and sheep red blood cells and several human tumor cell lines. See also, Elsbach and Weiss, 1981, *Advances in Inflammation Research,* ed. G. Weissmann, Vol. 2, pages 95–113, Raven Press. This reported target cell specificity was believed to be the result of the strong attraction of BPI for lipopolysaccharide (LPS), which is unique to the outer membrane (or envelope) of gram-negative organisms.

The precise mechanism by which BPI kills gram-negative bacteria is not yet known, but it is believed that BPI must first bind to the surface of the bacteria through electrostatic and hydrophobic interactions between the cationic BPI protein and negatively charged sites on LPS. LPS has been referred to as "endotoxin" because of the potent inflammatory response that it stimulates, i.e., the release of mediators by host inflammatory cells which may ultimately result in irreversible endotoxic shock. BPI binds to lipid A, reported to be the most toxic and most biologically active component of LPS. In susceptible gram-negative bacteria, BPI binding is thought to disrupt LPS structure, leading to activation of bacterial enzymes that degrade phospholipids and peptidoglycans, altering the permeability of the cell's outer membrane, and initiating events that ultimately lead to cell death. [Elsbach and Weiss, 1992, supra]. BPI is proposed to act in two stages. The first is a sublethal stage that is characterized by immediate growth arrest, permeabilization of the outer membrane and selective activation of bacterial enzymes that hydrolyze phospholipids and peptidoglycans. It has been reported that bacteria at this stage can be rescued by growth in serum albumin supplemented media (Mannion et al., 1990, *J. Clin. Invest.* 85: 853–860). The second stage, defined by growth inhibition that was not reversed by serum albumin, occurring after prolonged exposure of the bacteria to BPI and characterized by extensive physiologic and structural changes, including apparent damage to the inner cytoplasmic membrane.

Initial binding of BPI to LPS leads to organizational changes that probably result from binding to the anionic groups in the KDO region of LPS, which normally stabilize the outer membrane through binding of Mg$^{++}$ and Ca$^{++}$. Attachment of BPI to the outer membrane of gram-negative bacteria produces rapid permeabilization of the outer membrane to hydrophobic agents such as actinomycin D. Binding of BPI and subsequent gram-negative bacterial killing depends, at least in part, upon the LPS polysaccharide chain length, with long O-chain bearing, "smooth" organisms being more resistant to BPI bactericidal effects than short O-chain bearing, "rough" organisms (Weiss et al., 1980, *J. Clin. Invest.* 65: 619–628). This first stage of BPI action, permeabilization of the gram-negative outer envelope, is reversible upon dissociation of the BPI, a process requiring the presence of high divalent cations and synthesis of new LPS (Weiss et al., 1984, *J. Immunol.* 132: 3109–3115). Loss of gram-negative bacterial viability, however, is not reversed by processes which restore the envelope integrity, suggesting that the bactericidal action is mediated by additional lesions induced in the target organism and which may be situated at the cytoplasmic membrane (Mannion et al., 1990, *J. Clin. Invest.* 86: 631–641). Specific investigation of this possibility has shown that on a molar basis BPI is at least as inhibitory of cytoplasmic membrane vesicle function as polymyxin B (In't Veld et al., 1988, *Infection and Immunity* 56: 1203–1208) but the exact mechanism as well as the relevance of such vesicles to studies of intact organisms has not yet been elucidated.

Three separate functional domains within the recombinant 23 kD N-terminal BPI sequence have been discovered (Little et al., 1994, *J. Biol. Chem.* 269: 1865). These functional domains of BPI designate regions of the amino acid sequence of BPI that contributes to the total biological activity of the protein and were essentially defined by the activities of proteolytic cleavage fragments, overlapping 15-mer peptides and other synthetic peptides. Domain I is defined as the amino acid sequence of BPI comprising from about amino acid 17 to about amino acid 45. Initial peptides based on this domain were moderately active in both the inhibition of LPS-induced LAL activity and in heparin binding assays, and did not exhibit significant bactericidal activity. Domain II is defined as the amino acid sequence of BPI comprising from about amino acid 65 to about amino acid 99. Initial peptides based on this domain exhibited high LPS and heparin binding capacity and exhibited significant antibacterial activity. Domain III is defined as the amino acid sequence of BPI comprising from about amino acid 142 to about amino acid 169. Initial peptides based on this domain exhibited high LPS and heparin binding activity and exhibited surprising antimicrobial activity, including antifungal and antibacterial (including, e.g., anti-gram-positive and anti-gram-negative) activity. The biological activities of peptides derived from or based on these functional domains (i.e., functional domain peptides) may include LPS binding, LPS neutralization, heparin binding, heparin neutralization or antimicrobial activity.

Many utilities of BPI protein products, including $rBPI_{23}$ and $rBPI_{21}$, have been described due to the wide variety of biological activities of these products. For example, BPI protein products are bactericidal for gram-negative bacteria, as described in U.S. Pat. Nos. 5,198,541 and 5,523,288. International Publication No. WO 94/20130 proposes methods for treating subjects suffering from an infection (e.g. gastrointestinal) with a species from the gram-negative bacterial genus Helicobacter with BPI protein products. BPI protein products also enhance the effectiveness of antibiotic therapy in gram-negative bacterial infections, as described in U.S. Pat. No. 5,523,288 and International Publication No. WO 95/08344 (PCT/US94/11255). BPI protein products are also bactericidal for gram-positive bacteria and mycoplasma, and enhance the effectiveness of antibiotics in gram-positive bacterial infections, as described in U.S. Pat. Nos. 5,578,572 and 5,783,561 and International Publication No. WO 95/19180 (PCT/US95/00656). BPI protein products exhibit antifungal activity, and enhance the activity of other antifungal agents, as described in U.S. Pat. No. 5,627,153 and International Publication No. WO 95/19179 (PCT/US95/00498), and further as described for antifungal peptides in U.S. Pat. No. 5,858,974, which is in turn a continuation-in-part of U.S. application Ser. No. 08/504,841, abandoned, and corresponding International Publication Nos. WO 96/08509 (PCT/US95/09262) and WO 97/04008 (PCT/US96/03845). BPI protein products exhibit anti-protozoan activity, as described in U.S. Pat. No. 5,646,114 and International Publication No. WO 96/01647 (PCT/US95/08624). BPI protein products exhibit anti-chlamydial activity, as described in co-owned U.S. Pat. No. 5,888,973 and WO 98/06415 (PCT/US97/13810). Finally, BPI protein products exhibit anti-mycobacterial activity, as described in co-owned, co-pending U.S. application Ser. No. 08/626,646, now U.S. Pat. No. 6,214,789, which is in turn a continuation of U.S. application Ser. No. 08/285,803, abandoned, which is in turn a continuation-in-part of U.S. application Ser. No. 08/031,145 abandoned, and corresponding international Publication No. WO 94/20129 (PCT/US94/02463).

The effects of BPI protein products in humans with endotoxin in circulation, including effects on TNF, IL-6 and endotoxin are described in U.S. Pat. No. 5,643,875 and corresponding International Publication No. WO 95/19784 (PCT/US95/01151).

BPI protein products are also useful for treatment of specific disease conditions, such as meningococcemia in humans (as described in co-owned U.S. application Ser. No. 08/644,287, abandoned, and U.S. Pat. No. 5,888,977 and International Publication No. WO97/42966 (PCT/US97/08016), hemorrhagic trauma in humans, (as described in U.S. Pat. Nos. 5,756,464, 5,945,399, and corresponding International Publication No. WO 97/44056 (PCT/US97/08941), burn injury (as described in U.S. Pat. No. 5,494,896) ischemia/reperfusion injury (as described in U.S. Pat. No. 5,578,568), and liver resection (as described in co-owned, co-pending U.S. application Ser. No. 09/689,097, which is a continuation of U.S. application Ser. No. 09/466,412, abandoned, which is a continuation of U.S. application Ser. No. 08/582,230, abandoned, which is in turn a continuation of U.S. application Ser. No. 08/318,357, abandoned, which is in turn a continuation-in-part of U.S. application Ser. No. 08/132,510, abandoned, and corresponding International Publication No. WO 95/10297 (PCT/US94/11404).

BPI protein products also neutralize the anticoagulant activity of exogenous heparin, as described in U.S. Pat. No. 5,348,942, and are useful for treating chronic inflammatory diseases such as rheumatoid and reactive arthritis and for inhibiting angiogenesis and for treating angiogenesis-associated disorders including malignant tumors, ocular retinopathy and endometriosis, as described in U.S. Pat. Nos. 5,639,727, 5,807,818 and 5,837,678 and International Publication No. WO 94/20128 (PCT/US94/02401).

BPI protein products are also usefull in antithrombotic methods, as described in U.S. Pat. No. 5,741,779 and U.S. application Ser. No. 09/063,465, issued on Aug. 10, 1999 as U.S. Pat. No. 5,935,930, and corresponding International Publication No. WO 97/42967 (PCT/US7/08017).

Fungi are eukaryotic cells that may reproduce sexually or asexually and may be biphasic, with one form in nature and a different form in the infected host. Fungal diseases are referred to as mycoses. Some mycoses are endemic, i.e. infection is acquired in the geographic area that is the natural habitat of that fungus. These endemic mycoses are usually self-limited and minimally symptomatic. Some mycoses are chiefly opportunistic, occurring in immunocompromised patients such as organ transplant patients, cancer patients undergoing chemotherapy, burn patients, AIDS patients, or patients with diabetic ketoacidosis.

Fungal infections are becoming a major health concern for a number of reasons, including the limited number of antifungal agents available, the increasing incidence of species resistant to older antifungal agents, and the growing population of immunocompromised patients at risk for opportunistic fungal infections. The incidence of systemic fungal infections increased 600% in teaching hospitals and 220% in non-teaching hospitals during the 1980's. The most common clinical isolate is *Candida albicans* (comprising about 19% of all isolates). In one study, nearly 40% of all deaths from hospital-acquired infections were due to fungi. (Sternberg, 1994, *Science* 266: 1632–1634).

Neutropenic patients (due to, e.g., chemotherapy, immunosuppressive therapy, infection, including AIDS, or an otherwise dysfunctional immune system) are predisposed to the development of invasive fungal infections, most commonly including Candida species and Aspergillus species, and, on occasion, Fusarium, Trichosporon and Dreschlera. Cryptoccocus infection is also common in patients on immunosuppressive agents.

Antifungal agents include three main groups. The major group includes polyene derivatives, including amphotericin B and the structurally related compounds nystatin and pimaricin, which are only administered intravenously. These are broad-spectrum antifungals that bind to ergosterol, a component of fungal cell membranes, and thereby disrupt the membranes, leading to cell death. Amphotericin B is usually effective for systemic mycoses, but its administration is limited by toxic effects that include fever and kidney damage, and other accompanying side effects such as anemia, low blood pressure, headache, nausea, vomiting and phlebitis. The unrelated antifungal agent flucytosine (5-fluorocytosine), an orally absorbed drug, is frequently used as an adjunct to amphotericin B treatment for some forms of candidiasis and cryptococcal meningitis. Its adverse effects include bone marrow depression with leukopenia and thrombocytopenia.

The second major group of antifungal agents includes azole derivatives which impair synthesis of ergosterol and lead to accumulation of metabolites that disrupt the function of fungal membrane-bound enzyme systems (e.g., cytochrome P450) and inhibit fungal growth. Significant inhibition of mammalian P450 results in important drug interactions. This group of agents includes ketoconazole, clotrimazole, miconazole, econazole, butoconazole, oxiconazole, sulconazole, terconazole, fluconazole and itraconazole. These agents may be administered to treat systemic mycoses. Ketoconazole, an orally administered imidazole, is used to treat nonmeningeal blastomycosis, histoplasmosis, coccidioidomycosis and paracoccidioidomycosis in non-immunocompromised patients, and is also useful for oral and esophageal candidiasis. Adverse effects include rare drug-induced hepatitis; ketoconazole is also contraindicated in pregnancy. Itraconazole appears to have fewer side effects than ketoconazole and is used for most of the same indications. Fluconazole also has fewer side effects than ketoconazole and is used for oral and esophageal candidiasis and cryptococcal meningitis. Miconazole is a parenteral imidazole with efficacy in coccidioidomycosis and several other mycoses, but has side effects including hyperlipidemia and hyponatremia.

The third major group of antifungal agents includes allylamines-thiocarbamates, which are generally used to treat skin infections. This group includes tolnaftate and naftifine.

Another antifungal agent is griseofulvin, a fungistatic agent which is administered orally for fungal infections of skin, hair or nails that do not respond to topical treatment.

Most endemic mycoses are acquired by the respiratory route and are minimally symptomatic; cough, fever, headache, and pleuritic pain may be seen. Occasionally, endemic mycoses may cause progressive pulmonary disease or systemic infection. Histoplasmosis, caused by Histoplasma, is the most common endemic respiratory mycosis in the United States; over 40 million people have been infected. The disease is noncontagious and ordinarily self-limited, but chronic pulmonary infection and disseminated infection may occur. Pulmonary infection rarely requires treatment, but disseminated infection may be treated with amphotericin B. Coccidioidomycosis, caused by Coccidioides, is a noncontagious respiratory mycosis prevalent in the southwest United States. It also is usually self-limited but may lead to chronic pulmonary infection or disseminated infection. Amphotericin B or miconazole may be given for treatment. Blastomycosis, caused by Blastomyces is a noncontagious, subacute or chronic endemic mycosis most commonly seen in the southeast United States. Most pulmonary infections are probably self-limited. Patients with progressive lung disease or disseminated disease, and immunocompromised patients, may be treated systemically with amphotericin B. Paracoccidioidomycosis, caused by Paracoccidioides, is a noncontagious respiratory mycosis that is the most common systemic mycosis in South America. It may be acute and self-limited or may produce progressive pulmonary disease or extrapulmonary dissemination. Disseminated disease is generally fatal in the absence of therapy. Sulfonamides may be used but have a low success rate. Amphotericin B produces a higher response rate but relapses may still occur.

Cryptococcosis is a noncontagious, often opportunistic mycosis. It is characterized by respiratory involvement or hematogenous dissemination, often with meningitis. A major etiologic agent is *C. neoformans*. Most pulmonary infections are probably overlooked, but cryptococcal meningitis, which accounts for 90% of reported disease, is dramatic and seldom overlooked. Cryptococcosis is a particular problem in immunocompromised patients; cryptococcal meningitis occurs in 7 to 10% of AIDS patients. The principal symptom of meningitis is headache; associated findings include mental changes, ocular symptoms, hearing deficits, nausea, vomiting, and seizures. Without treatment, 80% of patients die within two years. In meningitis, cryptococci can be observed in India ink preparations of cerebrospinal fluid sediment, and can be cultured from the cerebrospinal fluid. Treatment is generally with fluconazole or the combination of amphotericin B and flucytosine, although amphotericin B does not cross the blood brain barrier.

Aspergillosis is a term that encompasses a variety of disease processes caused by Aspergillus species. Aspergillus species are ubiquitous; their spores are constantly being inhaled. Of the more than 300 species known, only a few are ordinarily pathogenic for man: *A. fumigatus, A. flavus, A. niger, A. nidulans, A. terreus, A. sydowi, A. flavatus,* and *A. glaucus*. Aspergillosis is increasing in prevalence and is particularly a problem among patients with chronic respiratory disease or immunocompromised patients. Among immunocompromised patients, aspergillosis is second only to candidiasis as the most common opportunistic mycosis and accounts for about 15% of the systemic mycoses in this group. Opportunistic pulmonary aspergillosis is characterized by widespread bronchial erosion and ulceration, followed by invasion of the pulmonary vessels, with thrombosis, embolization and infarction. Clinically, infection manifests as a necrotizing patchy bronchopneumonia, sometimes with hemorrhagic pulmonary infarction. In about 40% of cases, there is hematogenous spread to other sites. Aspergillosis is also a rare but devastating complication of burn wounds; amputation is often required for cure. Invasive aspergillosis is commonly fatal, so aggressive diagnosis and treatment is required. Blood, urine and cerebrospinal fluid cultures are rarely positive, but fungi can be seen in smears and biopsies. Amphotericin B can be given for treatment.

Dermatophytosis is a chronic fungal infection of the skin, hair or nails by dermatophytes, which include members of the species Trichophyton, Microsporum and Epidermophyton. Infection of the foot (tinea pedis), scalp (tinea capitis) are most common, although widespread infection on non-hair-bearing skin (tinea corporis) also occurs. Clinical manifestations vary and may present on the skin as fissuring or lesions with scaling, vesicles or pustules (and alopecia on the scalp), or on the nails as discolored or chalky, crumbling nails. Both topical and systemic therapies may be used to treat dermatophyte infection, including topically administered imidazoles and triazoles (such as itraconazole, miconazole, ketoconzaole and econzaole), haloprogin, undecylic acid, ciclopirox olamine, tolnaftate and terbinafine.

Fusarium species can cause localized or hematogenously disseminated infection (fusariosis), most frequently in patients who have a hemopoietic malignancy and neutropenia. Abrupt onset of fever, sometimes with myalgia, is followed in the majority of cases by distinctive skin lesions resembling ecthyma gangrenosum. Infection can be treated with amphotericin B but recovery depends ultimately on alleviation of neutropenia. Mortality typically exceeds 90%.

Mucormycosis is an acute suppurative opportunistic mycosis that produces rhinocerebral, pulmonary or disseminated disease in immuno-compromised patients, and local or disseminated disease in patients with burns or open wounds. Infection is caused by fungi in the class Zygomycetes, and include Basidiobolus, Conidiobolus, Rhizopus, Mucor, Absidia, Mortierella, Cunninghamella, and Saksenaea. Rhinocerebral mucormycosis accounts for about half of all cases of mucormycosis. It is one of the most rapidly fatal fungal diseases, with death occurring within 2–10 days in untreated patients. Early clinical signs include nasal stuffiness, bloody nasal discharge, facial swelling and facial pain. The infection then spreads to the eyes, cranial nerves and brain. Pulmonary mucormycosis is nearly as common as rhinocerebral disease and manifests with the same necrotizing and infarction as aspergillosis. Fungi are virtually never seen or cultured from blood, sputum or cerebrospinal fluid. Disseminated mucormycosis may follow pulmonary or burn wound infection. Treatment is with amphotericin B.

Candidiasis is a general term for a variety of local and systemic processes caused by colonization or infection of the host by species of the yeast Candida. Candidiasis occurs worldwide; superficial infections of the skin, mouth and other mucus membranes are universal. Invasive systemic disease has become a problem due to the use of high doses of antibiotics that destroy normal bacterial flora, immunosuppressive agents, and agents toxic to bone marrow, e.g., during cancer therapy. Neutropenia is a major risk factor for Candida dissemination. Candidiasis is also seen among immunocompromised individuals such as AIDS patients, organ transplant patients, patients receiving parenteral nutrition, and cancer patients undergoing radiation treatment and chemotherapy. It is the most common opportunistic mycosis in the world. The most common etiologic agent is *Candida albicans*. Other infectious species include *C. tropicalis, C. parapsilosis, C. stellatoidea, C. krusei, C. parakrusei, C lusitaniae, C. pseudotropicalis, C. guilliermondi* and *C. glabrata. Candida albicans* is normally found in the mouth, throat, gastrointestinal tract and vagina of humans. Non-albicans species frequently colonize skin. Candida species occur in two forms that are not temperature- or host-dependent. The usual colonizing forms are yeasts that may assume a pseudomycelial configuration, especially during tissue invasion. Pseudomyceliae result from the sequential budding of yeasts into branching chains of elongated organisms.

*Candida albicans* contains cell wall mannoproteins that appear to be responsible for attachment of the yeast cells to specific host tissues. It has been reported that the mannan portion, rather than the protein portion, of the mannoproteins is responsible for adherence of fungal cells to spleen and lymph node tissues in mice. (Kanbe et al., 1993, *Infection Immunity*, 61: 2578–2584).

*C. albicans* also binds avidly to extracellular matrix (ECM) proteins such as fibronectin, laminin, and types I and IV collagen, all of which contain heparin-binding domains. This suggests *C. albicans* may express a heparin-like surface molecule. Adherence of *C. albicans* to the ECM may be important in the pathogenesis of disseminated candidiasis. It has been demonstrated that heparin, heparan sulfate and dextran sulfate glycosaminoglycans (GAGs) inhibit adherence of *C. albicans* to ECM and ECM proteins, possibly by a mechanism involving binding of GAGs to ECM proteins, thus masling these selective ligands. (Klotz et al., 1992, *FEMS Microbiology Letters* 78: 205–208).

Clinically, candidiasis manifests as superficial mucocutaneous infections, chronic mucocutaneous candidiasis, or systemic infection. Superficial mucocutaneous infections can occur in any area of skin or mucus membrane. Thrush, commonly seen in AIDS patients, is characterized by a patchy or continuous, creamy to gray pseudomembrane that covers the tongue, mouth, or other oropharyngeal surfaces and may be accompanied by ulceration and necrosis. Laryngeal involvement results in hoarseness. Esophagitis is often an extension of oropharyngeal disease and may manifest with symptoms of retrostemal pain and dysphagia. Intestinal candidiasis is commonly asymptomatic, but is a major source of hematogenous invasion in immunocompromised individuals. Intertrigo involves the axillae, groins, inframammary folds, and other warm, moist areas, and may manifest as red, oozing or dry, scaly lesions. Infections may occur in other areas, including perianal and genital areas. Paronychia, infection of the nails, often follows chronic exposure of the hands or feet to moisture. Some patients with limited T-cell immunodeficiency develop chronic mucocutaneous candidiasis. These patients suffer from persistent superficial Candida infection of the skin, scalp, nails and mucus membranes.

Most cases of systemic candidiasis are caused by *Candida albicans* and *C. tropicalis,* and increasingly, *C. glabrata.* Clinical manifestations of Candida infection appear mainly in the eyes, kidneys and skin. In the eyes, there may be single or multiple raised, white, fluffy chorioretinal lesions. These lesions are a potential cause of blindness. Involvement of the kidneys includes diffuse abscesses, capillary necrosis and obstruction of the ureters. Infection may result in progressive renal insufficiency. Systemic Candida infection can also manifest as maculonodular skin lesions surrounded by a reddened area; these lesions have an appearance similar to acne but are a major clue to a potentially lethal disease. Other manifestations of systemic candidiasis may include osteomyelitis, arthritis, meningitis, and abscesses in the brain, heart, liver, spleen and thyroid.

Involvement of the lungs is also common, but pulmonary lesions are usually too small to be seen on chest X-ray. Finally, Candida endocarditis can occur in patients receiving prolonged intravenous therapy or cardiac valve implants, or in intravenous drug abusers. Fungal lesions appear on the valves, and can embolize and occlude large blood vessels.

Superficial infections are diagnosed by microscopic examination of scrapings or swabs of infected lesions in the presence of 10% potassium hydroxide. Candida organisms can also be seen on gram stain. Endocarditis is diagnosed by blood cultures or demonstration of bulky valvular lesions on echocardiography. Systemic candidiasis may be difficult to diagnose because the presence of heavy colonization at the usual sites of infection indicates, but does not prove, that dissemination has occurred. The most reliable evidence of systemic candidiasis is biopsy demonstration of tissue invasion or recovery of yeast from fluid in a closed body cavity, such as cerebral spinal fluid, pleural or peritoneal fluid. Similarly, positive blood or urine or sputum cultures may indicate invasive disease or simply localized disease around indwelling devices, e.g., catheters or intravenous lines.

Mucocutaneous infections may be treated with topical preparations of nystatin, amphotericin B, clotrimazole, miconazole, haloprogin or gentian violet. Oropharyngeal or esophageal candidiasis can be treated with systemic agents such as ketoconazole or fluconazole. Chronic mucocutaneous candidiasis syndrome may respond to topical or systemic therapeutic agents such as amphotericin B or ketoconazole, but often relapses when medication is discontinued. Cystitis may be treated with amphotericin B bladder rinses, or a brief low-dose intravenous course of amphotericin B with or without oral flucytosine. Endocarditis is essentially incurable without valve replacement, accompanied by a 6 to 10 week course of amphotericin B and flucytosine. Even with therapy, however, complete cure of endocarditis is not always possible.

The mortality rate from systemic candidiasis is about 50%. Systemic candidiasis may be treated with fluconazole, a fungistatic agent, or amphotericin B, a fungicidal agent although systemic use of the latter is limited by its toxicity. Both drugs have substantial adverse reactions when used in combination with cyclosporine A, which itself can be nephrotoxic. The removal of precipitating factors such as intravenous lines or catheters is also important for controlling infection. Flucytosine therapy can be added to the amphotericin B therapy for treatment of systemic candidiasis, especially in patients that are not immunocompromised. In immunocompromised patients, however, these infections are problematic and resist effective treatment. Mortality with systemic candidiasis can be over 90% in such patients. Furthermore, chronic mucocutaneous candidiasis and candidal endocarditis often show evidence of disease after having been declared cured.

Infection of the cornea and conjunctiva, including keratoconjunctivitis, can result from infection by amoeba, viruses, fungi and bacteria. Debilitated patients can develop keratitis from fungi such as Candida or Fusarium which is often associated with corneal ulceration and can lead to scarring with severe visual loss.

There continues to exist a need in the art for new products and methods for their use as antifungal agents. In particular, effective antifungal therapy for systemic mycoses is limited. Products and methods responsive to this need would ideally involve substantially non-toxic compounds available in large quantities. Ideal compounds would have a rapid effect and a broad spectrum of fungicidal or fungistatic activity against a variety of different fungal species when administered or applied as the sole antifungal agent. Ideal compounds would also be useful in combinative therapies with other antifungal agents, particularly where these activities would reduce the amount of antifungal agent required for therapeutic effectiveness, enhance the effect of such agents, or limit potential toxic responses and high cost of treatment. Particularly advantageous would be compounds that are orally available and active for administration of antifungal agents.

SUMMARY OF THE INVENTION

The present invention provides biologically active derivatized compounds and compositions of small peptide-based constructs with sequences derived from or based on Domain III (amino acids 142–169) of bactericidal/permeability-increasing protein (BPI) and therapeutic uses of such compounds, including as antifungal agents. Derivatized antifungal compounds of the invention are useful in methods of treating a subject suffering from a fungal infection by administering a therapeutically effective amount of the compound. This is based on the unexpected discovery that antifungal activity may be retained and/or enhanced by the derivatization. A second unexpected discovery is that such derivatized compounds may have increased cellular absorption leading to oral availability and activity. These derivatized compounds provide additional benefits for the treatment of fungal infections. Derivatized compounds may be administered alone or in conjunction with known antifungal agents. When made the subject of adjunctive therapy, the administration of derivatized antifungal compounds of the invention may reduce the total amount of antifungal agent needed for effective therapy, thus limiting potential toxic response and/or high cost of treatment. Administration of these compounds may also enhance the effect of known agents, accelerate the effect of such agents, or reverse resistance of fungi to such agents. Compounds according to the invention include peptide-based constructs that have been chemically derivatized with sequences set out in SEQ ID NOS: 53 to 54.

In addition, the invention provides a method of killing or inhibiting growth of fungi comprising contacting the fungi with a derivatized compound. This method can be practiced in vivo or in a variety of in vitro uses such as to decontaminate fluids and surfaces and to sterilize surgical and other medical equipment and implantable devices, including prosthetic joints and indwelling invasive devices.

A further aspect of the invention involves use of a derivatized compound for the manufacture of a medicament for treatment of a fungal infection. The medicament may include, in addition to such a derivatized Domain III derived compound, other chemotherapeutic agents such as antifungal agents.

The invention provides a compound with antifungal properties comprising a sequence having the formula:

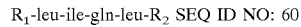

$R_1$-leu-ile-gln-leu-$R_2$ SEQ ID NO: 60 wherein,
$R_1$ is selected from the group consisting of $R_3$-, $R_3$-α-, or $R_3$-α-χ-;
$R_3$ is selected from the group consisting of H, CHO—, $CH_3CO$—, $R_4$—$CH_2$—, $R_4$—$CH_2$—CO—, $R_4$—CO—, $R_4$—$SO_y$—, or $R_4$—$PO_z$—; wherein, y=0–3, z=1–4;
$R_4$ is a hydrophobic moiety selected from the group consisting of a cyclic molecule having at least 3 carbon atoms, a heterocyclic molecule having at least 3 atoms, a functionalized cyclic molecule having at least 3 carbon atoms, or a functionalized heterocyclic molecule having at least three atoms;

α is a hydrophilic basic amino acid moiety selected from the group consisting of lysine, arginine, histidine, ornithine, diaminobutyric acid, citrulline, or para-amino phenylalanine;

χ is a hydrophobic amino acid moiety selected from the group consisting of alanine, naphthylalanine, biphenylalanine, valine, leucine, isoleucine, proline, hydroxyproline, phenylalanine, tryptophan, methionine, glycine, cyclohexylalanine, amino-isobutyric, norvaline, norleucine, tert-leucine, tetrahydroisoquinoline, pipecolic acid, phenylglycine, homophenylalanine, cyclohexylglycine, dehydroleucine, (2,2-diethylglycine), 1-amino-1-cyclopentane carboxylic acid, 1-amino-1-cyclohexane carboxylic acid, 2-amino-1-benzene carboxylic acid, 3-amino-1-benzene carboxylic acid, 3-amino-2-naphthene carboxylic acid, γ-amino butyric acid, β-alanine, difluorophenylalanine, para-fluorophenylalanine, nipecotic acid, amino butyric acid, thienyl-alanine, or t-butyl-glycine;

$R_2$ is selected from the group consisting of —$NH_2$, -χ-$NH_2$, -χ-α-$NH_2$, -χ-α-α-$NH_2$, -χ-α-α-α-$NH_2$,

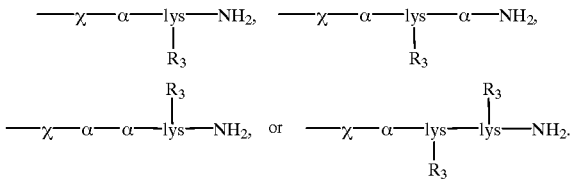

The invention further provides a compound with antifungal properties comprising a sequence having the formula:

$R_1$-ile-gln-leu-phe-$R_2$  SEQ ID NO: 61 wherein, $R_1$ is selected from the group consisting of $R_3$-, $R_3$-α-, $R_3$-α-χ-, or $R_3$-α-χ-χ-;

$R_3$ is selected from the group consisting of H, CHO—, $CH_3CO$—, $R_4$—$CH_2$—, $R_4$—$CH_2$—CO—, $R_4$—CO—, $R_4$—$SO_y$—, or $R_4$—$PO_z$—; wherein, y=0–3, z=1–4;

$R_4$ is a hydrophobic moiety selected from the group consisting of a cyclic molecule having at least 3 carbon atoms, a heterocyclic molecule having at least 3 atoms, a functionalized cyclic molecule having at least 3 carbon atoms, or a functionalized heterocyclic molecule having at least three atoms;

α is a hydrophilic basic amino acid moiety selected from the group consisting of lysine, arginine, histidine, ornithine, diaminobutyric acid, citulline, or para-amino phenylalanine;

χ is a hydrophobic amino acid moiety selected from the group consisting of alanine, naphthylalanine, biphenylalanine, valine, leucine, isoleucine, proline, hydroxyproline, phenylalanine, tryptophan, methionine, glycine, cyclohexylalanine, amino-isobutyric, norvaline, norleucine, tert-leucine, tetrahydroisoquinoline, pipecolic acid, phenylglycine, homophenylalanine, cyclohexylglycine, dehydroleucine, (2,2-diethylglycine), 1-amino-1-cyclopentane carboxylic acid, 1-amino-1-cyclohexane carboxylic acid, 2-amino-1-benzene carboxylic acid, 3-amino-1-benzene carboxylic acid, 3-amino-2-naphthene carboxylic acid, γ-amino butyric acid, β-alanine, difluorophenylalanine, para-fluorophenylalanine, nipecotic acid, amino butyric acid, thienyl-alanine, or t-butyl-glycine;

$R_2$ is selected from the group consisting of —$NH_2$, -α-$NH_2$, -α-α-$NH_2$, -α-α-α-$NH_2$,

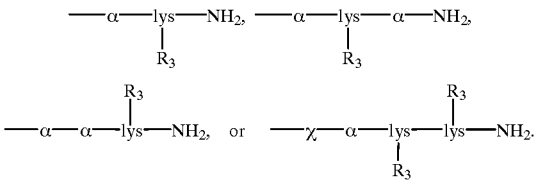

"Amino acid moieties" include typical and atypical amino acids (including derivatized and cyclized amino acids and amino acid analogs). "Conservative" substitutions of one amino acid for another are substitutions of amino acids having similar structural and/or chemical properties, and are generally based on similarities in polarity, charge, hydrophobicity, hydrophilicity and/or the amphipathic nature of the residues involved. Hydrophobic, polar neutral and polar basic amino acids include those described above for α, β and χ. Polar acidic amino acids include aspartic acid and glutamic acid. As a general rule, as the similarity between the amino acids being substituted decreases, the likelihood that the substitution will affect activity increases.

The invention also provides a compound selected from the group consisting of peptides of SEQ ID NOS: 1 through 52.

The invention further provides pharmaceutical compositions comprising the compounds of the invention and a pharmaceutically acceptable diluent, including compositions for oral administration, topical administration, and opththalmic administration.

Biologically active compounds of the invention may antimicrobial activity, including activity against gram-positive bacteria and/or antifungal activity. Biologically active compounds of the invention preferably have an epithelial absorption of at least about 0.001%, or more preferably at least about 0.01%, at least about 0.1%, at least about 1%, at least about 10%, at least about 20%, or more.

The invention also provides methods of treating subjects in need thereof, including subjects suffering from a fungal infection (e.g., involving infection by a fungal species selected from the group consisting of Candida, Aspergillus, Cryptococcus, Histoplasma, Coccidioides, Blastomyces, Basidiobolus, Conidiobolus, Rhizopus, Rhizomucor, Mucor, Absidia, Mortierella, Cunninghamella, Saksenaea, Fusarium, Trichophyton, Trichosporon, Microsporum, Epidermophyton, Scytalidium, Malassezia, Actinomyceies, Sporothrix and Penicillium) by administering a therapeutically effective amount of such compounds or compositions.

The invention further provides methods of prophylactically or therapeutically treating an immunocompromised subject comprising the step of administering to said subject an amount of the pharmaceutical composition of claim 6 effective to kill or inhibit replication of microbes, including fungi.

According to the treatment methods of the invention, concurrent administration of another non-BPI-derived antimicrobial agent, including antifungal agents.

Another aspect of the invention provides methods for identifying a derivatized peptide sequence derived from or based on the sequence of Domain III of bactericidal/ permeability-increasing protein (BPI) having antimicrobial properties and epithelial absorption of at least 0.001 % comprising the steps of:

(a) derivatizing a peptide sequence based on a sequence, subsequence, reverse sequence or reverse subsequence of Domain III of BPI through covalent linkage of a hydrophobic moiety or moieties at the N-terminus, C-terminus or within said peptide sequence;

(b) measuring the antimicrobial activity of said derivatized peptide sequence obtained in step (a); and (c) measuring the epithelial absorption of said derivatized peptide sequence obtained in step (a).

Peptide sequences suitable for derivatization in step (a) are MinLARPS.

Such methods include a method for designing and identifying an antimicrobial derivatized peptide sequence, prophylactic or therapeutic medicament derived from or based on the peptide sequence of BPI or a fragment thereof with epithelial absorption of at least 0.001%, said method comprising the steps of:

(a) identifying a target peptide sequence derived from or based on the polypeptide sequence of BPI or a fragment thereof which exhibits antimicrobial activity in vitro or in vivo;

(b) constructing a library of minimum length, activity retaining peptide sequences (MinLARPS) by substituting or deleting amino acid residues within said target peptide sequence;

(c) measuring the antimicrobial activity of said MinLARPS to determine the minimum number of residues necessary to retain antimicrobial activity of at least 1% of that of said target polypeptide sequence;

(d) measuring epithelial absorption of said MinLARPS in in vivo or in vitro assays to identify which of said MinLARPS retain epithelial absorption of at least 0.001%;

(e) synthesizing derivatized MinLARPS by chemically modifying said MinLARPS through covalent linkage of a hydrophobic moiety or moieties linked at the N-terinus, C-terminus, or within the sequence of said MinLARPS;

(f) repeating steps (c) and (d) with said derivatized MinLARPS.

DETAILED DESCRIPTION OF THE INVENTION

The present invention relates to novel derivatized peptide-based constructs and the unexpected discovery that the antifungal activity of the underivatized constructs is retained and/or enhanced in the derivatives. Preferred derivatives also have enhanced cellular absorption leading to oral availability and activity. Antifungal derivative compounds according to the invention can be administered to treat subjects suffering from fungal infection. "Treatment" as used herein encompasses both prophylactic and therapeutic treatment. As used herein, "subject" is meant to refer to higher organisms, including animals (e.g., humans; companion animals such as dogs; livestock such as horses, cows and pigs; poultry; insects; fish; avian species) and plants.

Domain III derived peptides were previously demonstrated to have antifungal activities both in in vitro killing assays and in in vivo models of fungal infection, as measured, for example, by improved survival or reduction of colony-forming units in circulation after fungal challenge (see, e.g., U.S. Pat. Nos. 5,627,153 and 5,858,974. A variety of fungal infections, including infections caused by Aspergillus, infections caused by Cryptococcus, such as cryptococcal meningitis, and mucocutaneous and systemic candidiasis caused by Candida species, may be treated according to the invention. In addition, Domain III derived peptides were demonstrated to have LPS-neutralizing activity both in an in vitro assay and an in vivo model. This activity provides an additional benefit in the treatment of fungal infections where bacterial LPS from translocation or additional infection is associated with the fungal infection.

As used herein, "Domain III derived peptide" includes peptides having an amino acid sequence of BPI protein from about position 142 to about position 169, subsequences thereof and variants of the sequence or subsequence thereof, which possess antifungal activity. Specifically included are those antifungal peptides having six to fourteen amino acids and having the amino acid sequence of BPI protein from about position 148 to about position 161, subsequences thereof and variants of the sequence or subsequence. Certain preferred peptides have fourteen amino acids and among the preferred variant sequences and subsequences are those having K as an amino acid substituted for G at position 152. Preferred peptide sequences with fourteen amino acids have a core amino acid sequence. Preferred variant sequence peptides include those wherein at least one and most preferably two of each BPI L-amino acid sequence residue on the N- and C-termini has been replaced by a D-isomer amino acid. Variants involving BPI sequence replacements by atypical amino acids (e.g., β(1-naphthyl)A, β(2-naphthyl)A, para-amino F, cyclohexyl A, α- and γ-aminobutyric acids, α methyl A and N-methyl G, V and L) are also included within this group.

Preferred Domain III derived antifungal peptides of the invention have from seven to twelve amino acids comprising: (a) a core sequence of amino acids selected from the group consisting of LIQL (SEQ ID NO: 55), IQLF (SEQ ID NO: 56), WLIQL (SEQ ID NO: 57), LIQLF (SEQ ID NO: 58) and WLIQLF (SEQ ID NO: 59); and (b) one or more cationic amino acids selected from the group consisting of K, R, H, ornithine and diaminobutyric acid at the amino and/or carboxy terminal portion of the core sequence. A subset of peptides have from seven to nine amino acids comprising: (a) a core sequence of amino acids selected from the group consisting of LIQL (SEQ ID NO:55) and IQLF (SEQ ID NO: 56); and (b) at least two cationic amino acids selected from the group consisting of K, R, H, ornithine and diaminobutyric acid at the amino and/or carboxy terminal portion of the core sequence. Another subset of peptides has from eight to ten amino acids comprising: (a) a core sequence of amino acids selected from the group consisting of LIQLF (SEQ ID NO: 58) and WLIQLF (SEQ ID NO: 59); and (b) at least two cationic amino acids selected from the group consisting of K, R, H, ornithine and diaminobutyric acid at the amino and/or carboxy terminal portion of the core sequence. Still another subset of peptides has nine to twelve amino acids comprising: (a) a core sequence of amino acids selected from the group consisting of WLIQLF (SEQ ID NO:59); and (b) at least three cationic amino acids selected from the group consisting of K, R, H, ornithine and diaminobutyric acid at the amino and/or carboxy terminal portion of the core sequence.

It will be apparent from consideration of the structures of the above-described peptides that the Domain III sequence of BPI amino acids from 148 to 161 includes the core sequence(s) noted above as well as multiple cationic residues (K and H) flanking the core. This motif is carried forward in the structures of subsequences of the 148 to 161 sequence providing antifungal peptides of the invention and also preserved in antifungal variants of the 148 to 161 sequence and subsequences thereof. Note, for example that when the G residue normally in the BPI sequence at position 152 is replaced by K, this replacement serves to provide a cationic residue immediately adjacent to the predominantly hydrophobic core residues. Sequence and subsequence variants providing Domain m derived antifungal peptides thus include those peptides wherein one or more existing non-cationic residues ordinarily flanking the core sequence(s) are replaced by cationic residues.

Within the core sequence(s), the neutral aliphatic residues L and I are each replaceable by neutral aliphatic residues (e.g., G, A, V, I and L). Likewise, the aromatic residues W (BPI position 153) and F (BPI position 158) are replaceable by a different aromatic amino acid residues or by neutral aliphatic residues (e.g., G, A, V, I and L). Moreover, the core sequence Q (BPI residue 156) is replaceable preferably by a neutral hydrophilic amino acid (e.g., T, S and N). As noted above, where variations are introduced into core subsequence(s), it is preferable that the variant core sequence(s) retain 75% homology to the sequences occurring in BPI.

Preferred antifungal Domain III peptides have one or more D-isomer amino acids, and have the core sequence amino acids comprise L-isomer or D-isomer amino acids in reverse sequence order. The antifungal peptides can have an acetylated amino terminal amino acid residue. Cyclic antifungal peptides are also included.

Novel compounds and compositions of the present invention include small peptide-based constructs of 4–10 amino acid moieties in length of L-isomer and/or D-isomer amino acid moieties (included in the MinLARPS as explained below) that are based on or derived from subsequences or reverse subsequences from functional Domain III (amino acids 142–169) of BPI and which are chemically derivatized at specific targeted locations resulting in a designed molecule which exhibits enhanced epithelial cell absorption and potent biological activity. Such compounds are particularly desirable for oral administration.

The present invention discloses the strategy employed in selecting various classes of hydrophobic moieties and the strategic placement thereof within the peptide-based constructs for making and synthesizing compounds and compositions that are chemically-derivatized and biologically active peptide-based sequences. The present invention also provides methods for screening for the novel compounds and compositions for antifungal activity and enhanced levels of epithelial cell absorption. The present invention further provides compound and composition constructs designed to have enhanced epithelial cell absorption and antifungal activity.

Peptide-based constructs according to the invention were strategically designed to be of minimum length of amino acid moieties, while still retaining antifungal activity. Accordingly, a series of specifically targeted deletions and substitutions, with occasional additions were made to amino acids within a peptide sequence shown to have antifungal activity in order to determine minimum length, activity retaining peptide sequences (MinLARPS). The strategy employed in efforts to elucidate the MinLARPS was that the peptide sequences of minimum length would have higher epithelial cell absorption than a longer sequence. The resulting library of peptide sequences were synthesized, purified according to the methodology described herein and then initially screened in vitro for antimicrobial activity, preferably antifungal activity in, for example, radial diffusion assays and broth microdilution assays. Peptide sequences were also assayed for levels of epithelial cell absorption.

Specific areas of the MinLARPS were then targeted for chemical derivatization with hydrophobic moieties in order to facilitate epithelial cell absorption. The possible permutations of derivatization were extensive but the resulting chemistry employed yielded results wherein it was determined that the most favorable area of targeting derivatization on the MinLARPS which also yielded compounds with antifungal activity and epithelial cell absorption, were lysine amino acid residues located N-terminally or C-terminally. Nontrivially, N-terminal or C-terminal derivatization of amino acid moieties was initially to provide the most favorable retention of antifungal activity while enhancing epithelial cell absorption. Further studies revealed that favorable targets of derivatization from the library of MinLARPS were through C-terminal lysines and N-terminal lysines. Derivatization at the C-terminal portion of the MinLARPS was through the ε-amino group of lysine(s), while the C-terminus itself was generally amidated to protect from protease attack. Conversely, the studies yielded that favorable N-terminal derivatization of the MinLARPS was through the α-amino group of the N-terminal lysine. Independent of location, derivatization was found to achieve most favorable results when proceeding via introduction of specific hydrophobic moieties with acid group(s) attached and reacting with the MinLARPS for amino group attack on the activated acid(s) in an $S_n2$ reaction mechanism. Further description of the synthesis is described in detail herein. The resulting chemically-derivatized MinLARPS were then assayed for retention of antifungal activity and enhanced epithelial cell absorption. Constructs according to the invention were based on the formula:

$$R_1\text{-leu-ile-gln-leu-}R_2 \text{ (SEQ ID NO: 60)}$$

wherein $R_1$, the N-terminal expander, is selected from the group consisting of $R_3$-, $R_3$-α-, or $R_3$-α-χ-. $R_3$ is a linker group selected from the group consisting of H, CHO—, $CH_3CO$—, $R_4$—$CH_2$—, $R_4$—$CH_2$—CO—, $R_4$—CO—, $R_4$—$SO_y$—, or $R_4$—$PO_z$—, wherein y=0–3 and z=1–4. $R_4$ is a hydrophobic moiety selected from the group consisting of a cyclic molecule having at least 3 carbon atoms, a heterocyclic molecule having at least 3 atoms, a functionalized cyclic molecule having at least 3 carbon atoms, or a functionalized heterocyclic molecule having at least three atoms. The present invention discloses $R_4$ to include a hydrophobic moiety selected from the group consisting of biotin, 2-biphenylene, 2-anthraquinone, 2-benzofuran, 2-indole, 1-isoquinoline, hydroxyphenyl, 2-quinoline, 1-[3-(3,4-dihydroxycinnamoyl)-1,3,4,5-tetrahydroxycyclohexane], 1-(3,5-dichloro-2-hydroxyphenyl), 1-(3,5-diiodo-2-hydroxyphenyl), 1-(3,5-dinitro-2-hydroxyphenyl), 1-(4-azido-2-hydroxyphenyl), 4-biphenyl, 2-biphenyl, 1-naphthyl, 2-naphthyl, 3-amino-2-naphthyl, 3-chloro-2-nitrophenyl, (3,4-dihydroxyphenyl), 3,4,5-trihydroxyphenyl, 2-chloro-3-nitrophenyl, 5-azido-2-nitrophenyl, 3-amino-2-pyrazine, 2-benzyloxycarbonyl-ethyl, 2-thiophene, 2-(3,4-dihydroxyphenyl)ethene, 5-bromo-3-indolemethylene, 2-(4-hydroxy-3-methoxyphenyl)ethene, 2-(3-chlorophenyl)ethene, 2-pyrazine, 4-imidazole, 2-imino-1-imidazolidine, pyridine, 3-piperidine, 4-piperidine, fluorescein, 2-(4-amino-3,5,6-trichloro-pyridine), and 3-(2-chloro-6-fluorophenyl)-5-methylisoxazole.

α is a hydrophilic basic amino acid moiety selected from the group consisting of lysine, arginine, histidine, ornithine, diaminobutyric acid, citrulline, or para-anlino phenylalanine. χ is a hydrophobic amino acid moiety selected from the group consisting of alanine, naphthylalanine, biphenylalanine, valine, leucine, isoleucine, proline, hydroxyproline, phenylalanine, tryptophan, methionine, cysteine, glycine, cyclohexylalanine, amino-isobutyric, norvaline, norleucine, tert-leucine, tetrahydroisoquinoline, pipecolic acid, phenylglycine, homophenylalanine, cyclohexylglycine, dehydroleucine, (2,2-diethylglycine), 1-amino-1-cyclopentane carboxylic acid, 1-amino-1-cyclohexane carboxylic acid, 2-amino-1-benzoic acid, 3-amino-1-benzoic acid, 3-amino-2-naphthoic acid, γ-amino butyric acid, β-alanine, difluorophenylalanine, para-fluorophenylalanine, nipecotic acid, amino butyric acid, thienyl-alanine, or t-butyl-glycine. $R_2$, the C-terminal expander, is selected from the group consisting of —$NH_2$, -χ-$NH_2$, -χ-α-$NH_2$, -χ-α-α-$NH_2$, -χ-α-α-α-$NH_2$,

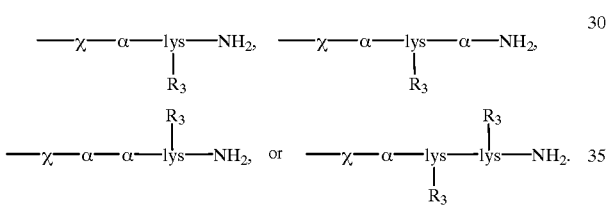

The second primary derivatized constructs were of the formula:

$R_1$-ile-gln-leu-phe-$R_2$ (SEQ ID NO: 61)

wherein $R_1$, the N-terminal expander, is selected from the group consisting of $R_3$-, $R_3$-α-, $R_3$-α-χ-, or $R_3$-α-χ-χ-. $R_3$ is of the same group of linkers described above. $R_4$ is from the same group of hydrophobic moieties listed above. α and χ are of the same character and selected from the same corresponding groups as set forth above. $R_2$, the C-terminal expander, is selected from the group consisting of —$NH_2$, -α-$NH_2$, -α-α-$NH_2$, -α-α-α-$NH_2$,

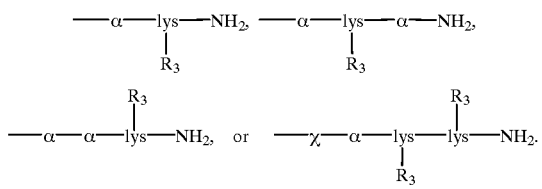

Other linking groups, $R_3$, and other chemistry of derivatization contemplated by the present invention can be carried out by those of ordinary skill in the art. Similarly, other hydrophobic moiety derivitization groups $R_4$, known in the art, are also contemplated by the present invention.

Peptide-based constructs included herein include:

| | |
|---|---|
| XMP.365 | SEQ ID NO: 1 |
| XMP.366 | SEQ ID NO: 2 |
| XMP.416 | SEQ ID NO: 3 |
| XMP.424 | SEQ ID NO: 4 |
| XMP.446 | SEQ ID NO: 5 |
| XMP.447 | SEQ ID NO: 6 |
| XMP.459 | SEQ ID NO: 7 |
| XMP.466 | SEQ ID NO: 8 |
| XMP.475 | SEQ ID NO: 9 |
| XMP.486 | SEQ ID NO: 10 |
| XMP.488 | SEQ ID NO: 11 |
| XMP.489 | SEQ ID NO: 12 |
| XMP.492 | SEQ ID NO: 13 |
| XMP.493 | SEQ ID NO: 14 |
| XMP.496 | SEQ ID NO: 15 |
| XMP.499 | SEQ ID NO: 16 |
| XMP.500 | SEQ ID NO: 17 |
| XMP.501 | SEQ ID NO: 18 |
| XMP.502 | SEQ ID NO: 19 |
| XMP.503 | SEQ ID NO: 20 |
| XMP.504 | SEQ ID NO: 21 |
| XMP.516 | SEQ ID NO: 22 |
| XMP.517 | SEQ ID NO: 23 |
| XMP.518 | SEQ ID NO: 24 |
| XMP.519 | SEQ ID NO: 25 |
| XMP.520 | SEQ ID NO: 26 |
| XMP.521 | SEQ ID NO: 27 |
| XMP.522 | SEQ ID NO: 28 |
| XMP.523 | SEQ ID NO: 29 |
| XMP.524 | SEQ ID NO: 30 |
| XMP.525 | SEQ ID NO: 31 |
| XMP.526 | SEQ ID NO: 32 |
| XMP.527 | SEQ ID NO: 33 |
| XMP.532 | SEQ ID NO: 34 |
| XMP.533 | SEQ ID NO: 35 |
| XMP.534 | SEQ ID NO: 36 |
| XMP.535 | SEQ ID NO: 37 |
| XMP.536 | SEQ ID NO: 38 |
| XMP.545 | SEQ ID NO: 39 |
| XMP.546 | SEQ ID NO: 40 |
| XMP.560 | SEQ ID NO: 41 |
| XMP.565 | SEQ ID NO: 42 |
| XMP.596 | SEQ ID NO: 43 |
| XMP.599 | SEQ ID NO: 44 |
| XMP.600 | SEQ ID NO: 45 |
| XMP.601 | SEQ ID NO: 46 |
| XMP.606 | SEQ ID NO: 47 |
| XMP.618 | SEQ ID NO: 48 |
| XMP.620 | SEQ ID NO: 49 |
| XMP.642 | SEQ ID NO: 50 |
| XMP.653 | SEQ ID NO: 51 |
| XMP.678 | SEQ ID NO: 52 |

Pharmaceutical compositions of the invention comprise a compound with antifungal properties with a sequence having the formula $R_1$-leu-ile-gln-leu-$R_2$ (SEQ ID NO:60) or $R_1$-ile-gln-leu-phe-$R_2$ (SEQ ID NO:61) as defined herein and a pharmaceutically acceptable diluent, adjuvant or carrier and are administered topically, intravenously, orally or as an aerosol.

In vitro methods of the invention permit killing or inhibiting replication of fungi through contacting the fungi with or pharmaceutical composition containing the same. Fungal infection treatment methods of the invention comprise administering to a subject suffering from a fungal infection a therapeutically effective amount of a compound according to the invention and such treatment methods are applicable to infections by fungal infection, including infection by Candida (especially, *C. albicans, C. glabrata, C. krusei, C. lusitaniae, C. parapsilosis* and *C. tropicalis*), Aspergillus and Cryptococcus species and others listed below. Therapeutically effective amounts include amounts effective to inhibit replication of or kill fungi.

Administration of such derivative compounds may be especially beneficial in immunocompromised patients, including immunosuppressed and neutropenic patients, e.g., patients undergoing chemotherapy, radiation therapy, or immunosupressive therapy, or patients with a dysfunctional immune system secondary to infection, such as HIV infection, or other causes. Topical administration of derivative compounds of the invention is also expected to be effective for treating, e.g., skin and eye infections, including those caused by dermatophytes.

Medicaments/pharmaceutical compositions developed according to the invention can include other antifungal agents including non-peptide agents or can be used in combinative therapeutic methods with other such agents.

Peptides derived from or based on BPI produced by recombinant or synthetic means (BPI-derived peptides) have been described in co-owned and co-pending PCT Application No. US94/10427 [WO 95/19372], which corresponds to U.S. Pat. No. 5,652,332, and PCT Application No. US94/02465 [WO 94/20532], which corresponds to U.S. Pat. Nos. 5,733,872 and 5,763,567, and PCT Application No. US94/02401 [WO 94/20128] and U.S. Pat. Nos. 5,348,942; 5,639,727; and 5,807,818. BPI-derived peptides having an amino acid sequence of BPI protein from about position 142 to about position 169, subsequences thereof and variants of the sequence or subsequence thereof, which possess a BPI antifungal biological activity, were disclosed in co-owned PCT Application No. US95/09262 [WO 96/08509] and PCT Application No. US96/03845 [WO 97/04008] and U.S. Pat. No. 5,858,974.

For purposes of this invention, the term "biological activity of BPI" is intended to include, but is not limited to one or more of the biological activities or properties of a human bactericidal/permeability-increasing (BPI) protein product, including, for example, a recombinant BPI holoprotein such rBPI (SEQ ID NO: 13), an amino-terminal fragment of BPI such as $rBPI_{23}$, and analogs that are mutated amino-terminal fragments of BPI such as $rBPI_{21}\Delta cys$ and including any of the known activities of the BPI protein products discussed above. Specifically included is a biological activity of any peptide-based construct of this invention that is between 0.1 and 10 times the activity of BPI or of a corresponding peptide encompassing a corresponding functional domain of BPI. The term "biological activity of BPI" is intended to include, but is not limited to an activity of heparin binding, heparin neutralization, inhibition of endothelial cell proliferation or inhibition of angiogenesis (e.g., inhibition of in vivo neovascularization such as that associated with metastatic tumors and chronic inflammatory disease states). Also included in this definition of "biological activity of BPI" is an activity of LPS binding, LPS neutralization, or antimicrobial activity. Also expressly included in this definition of the "biological activity of BPI" is a biological activity, for example antimicrobial activity, that is qualitatively different than the activity of BPI or the corresponding peptide encompassing the entire corresponding domain of BPI. For example, such qualitative differences include differences in the spectrum of bacteria or other microorganisms against which the peptide is effective, relative to the amino acid sequence of the corresponding functional domain of BPI. This definition thus encompasses antimicrobial activities, such as antibacterial activity (e.g., against gram-positive bacteria (including Staphylococcus, Streptococcus, Micrococcus, Peptococcus, Peptostreptococcus, Enterococcus, Bacillus, Clostridium, Lactobacillus, Listeria, Erysipelothrix, Propionibacterium, Eubacterium and Corynebacterium), mycobacteria and chlamydia) and antifungal activity (e.g., against species of Candida, Aspergillus, Cryptococcus, Histoplasma, Coccidioides, Blastomyces, Basidiobolus, Conidiobolus, Rhizopus, Rhizomucor, Mucor, Absidia, Mortierella, Cunninghamella, Saksenaea, Fusarium, Trichophyton, Trichosporon, Microsporum, Epidermophyton, Scytalidium, Malassezia, Actinomyceies, Sporothrix and Penicillium).

The administration of BPI protein products is preferably accomplished with a pharmaceutical composition comprising a BPI protein product and a pharmaceutically acceptable diluent, adjuvant, or carrier. The BPI protein product may be administered without or in conjunction with known surfactants or other therapeutic agents. A stable pharmaceutical composition containing BPI protein products (e.g., $rBPI_{23}$) comprises the BPI protein product at a concentration of 1 mg/ml in citrate buffered saline (5 or 20 mM citrate, 150 mM NaCl, pH 5.0) comprising 0.1% by weight of poloxamer 188 (Pluronic F-68, BASF Wyandotte, Parsippany, N.J.) and 0.002% by weight of polysorbate 80 (Tween 80, ICI Americas Inc., Wilmington, Del.). Another stable pharmaceutical composition containing BPI protein products (e.g., $rBPI_{21}$) comprises the BPI protein product at a concentration of 2 mg/ml in 5 mM citrate, 150 mM NaCl, 0.2% poloxamer 188 and 0.002% polysorbate 80. Such preferred combinations are described in U.S. Pat. Nos. 5,488,034 and 5,696,090 and corresponding International Publication No. WO 94/17819 (PCT/US94/01239). As described in U.S. Pat. No. 5,912,228, which is in turn a continuation-in-part of U.S. application Ser. No. 08/530,599, abandoned which is in turn a continuation-in-part of U.S. application Ser. No. 08/372,104, abandoned and corresponding International Publication No. WO 96/21436 (PCT/US96/01095), other poloxamer formulations of BPI protein products with enhanced activity may be utilized. Peptide-based constructs may be formulated like other BPI protein products or may be formulated in saline or a physiological buffer.

A derivative compound according to the invention may be administered systemically or topically. Systemic routes of administration include oral, intravenous, intramuscular or subcutaneous injection (including into depots for long-term release), intraocular or retrobulbar, intrathecal, intraperitoneal (e.g. by intraperitoneal lavage), transpulmonary using aerosolized or nebulized drug, or transdermal. Topical routes include administration in the form of salves, ophthalmic drops, ear drops, or irrigation fluids (for, e.g., irrigation of wounds).

When given parenterally, BPI protein product compositions are generally injected in doses ranging from 1 g/kg to 100 mg/kg per day, preferably at doses ranging from 0.1 mg/kg to 20 mg/kg per day. The treatment may continue by continuous infusion or intermittent injection or infusion, at the same, reduced or increased dose per day for, e.g., 1 to 3 days, and additionally as determined by the treating physician.

Those skilled in the art can readily optimize effective dosages and administration regimens for therapeutic compositions comprising BPI protein product (including the constructs of the present invention), as determined by good medical practice and the clinical condition of the individual subject.

A derivative compound according to the invention may be administered in conjunction with other antifungal agents, including azole derivatives such as the imidazoles and triazoles (e,g., ketoconazole, clotrimazole, miconazole, econazole, butoconazole, oxiconazole, sulconazole, terconazole, fluconazole and itraconazole); amphotericin B, nystatin and pimaricin; flucytosine (5-fluorocytosine); allylamines-thiocarbamates, such tolnaftate and naftifine; griseo fulvin, haloprogin, undecylic acid, ciclopirox olamine, tolnaftate and terbinafine.

Concurrent administration of a derivative compound according to the invention with antifungal agents is expected to improve the therapeutic effectiveness of the antifungal agents. This may occur through reducing the concentration of antifungal agent required to eradicate or inhibit fungal growth, e.g., replication. Because the use of some agents is limited by their systemic toxicity or prohibitive cost, lowering the concentration of antifungal agent required for therapeutic effectiveness reduces toxicity and/or cost of treatment, and thus allows wider use of the agent. Concurrent administration of a derivative compound according to the invention and another antifungal agent may produce a more rapid or complete fungicidal/fungistatic effect than could be achieved with either agent alone. Administration of a derivative compound according to the invention may reverse the resistance of fungi to antifungal agents. Administration of a derivative compound according to the invention may also convert a fungistatic agent into a fungicidal agent.

An advantage provided by the present invention is the ability to treat fungal infections, particularly Candida infections, that are presently considered incurable. Another advantage is the ability to treat fungi that have acquired resistance to known antifungal agents. A further advantage of concurrent administration of a derivative compound according to the invention with an antifungal agent having undesirable side effects, e.g., amphotericin B, is the ability to reduce the amount of antifungal agent needed for effective therapy. The present invention may also provide quality of life benefits due to, e.g., decreased duration of therapy, reduced stay in intensive care units or reduced stay overall in the hospital, with the concomitant reduced risk of serious nosocomial (hospital-acquired) infections.

"Concurrent administration" as used herein includes administration of the agents together, simultaneously or before or after each other. A derivative compound according to the invention and antifungal agents may be administered by different routes. For example, the derivative compound may be administered intravenously while the antifungal agents are administered intramuscularly, intravenously, subcutaneously, orally or intraperitoneally. Alternatively, the derivative compound may be administered intraperitoneally while the antifungal agents are administered intraperitoneally or intravenously, or the derivative compound may be administered in an aerosolized or nebulized form while the antifungal agents are administered, e.g., intravenously. The derivative compound and antifungal agents may be both administered orally. The derivative compound and antifungal agents may be given sequentially in the same intravenous line, after an intermediate flush, or may be given in different intravenous lines. The derivative compound and antifungal agents may be administered simultaneously or sequentially, as long as they are given in a manner sufficient to allow both agents to achieve effective concentrations at the site of infection.

Concurrent administration of derivative compound and another antifungal agent is expected to provide more effective treatment of fungal infections. Concurrent administration of the two agents may provide greater therapeutic effects in vivo than either agent provides when administered singly. For example, concurrent administration may permit a reduction in the dosage of one or both agents with achievement of a similar therapeutic effect. Alternatively, the concurrent administration may produce a more rapid or complete fungicidal/fungistatic effect than could be achieved with either agent alone.

Therapeutic effectiveness is based on a successful clinical outcome, and does not require that the antifungal agent or agents kill 100% of the organisms involved in the infection. Success depends on achieving a level of antifungal activity at the site of infection that is sufficient to inhibit the fungi in a manner that tips the balance in favor of the host. When host defenses are maximally effective, the antifungal effect required may be minimal. Reducing organism load by even one log (a factor of 10) may permit the host's own defenses to control the infection. In addition, augmenting an early fungicidal/fungistatic effect can be more important than long-term fungicidal/fungistatic effect. These early events are a significant and critical part of therapeutic success, because they allow time for host defense mechanisms to activate.

A derivative compound according to the invention may interact with a variety of host defense elements present in whole blood or serum, including complement, p15s and LBP, and other cells and components of the immune system. Such interactions may result in potentiation of the activities of the peptide. Because of these interactions, a derivative compound according to the invention can be expected to exert even greater activity in vivo than in vitro. Thus, while in vitro tests are predictive of in vivo utility, absence of activity in vitro does not necessarily indicate absence of activity in vivo. For example, BPI has been observed to display a greater bactericidal effect on gram-negative bacteria in whole blood or plasma assays than in assays using conventional media. (Weiss et al., 1992, *J. Clin. Invest.* 90: 1122–1130). This may be because conventional in vitro systems lack the blood elements that facilitate or potentiate BPI's function in vivo, or because conventional media contain higher than physiological concentrations of magnesium and calcium, which are typically inhibitors of the activity of BPI protein products. Furthermore, in the host, a derivative compound according to the invention are available to neutralize translocation of gram-negative bacteria and concomitant release of endotoxin, a further clinical benefit not seen in or predicted by in vitro tests of antifungal activity.

It is also contemplated that the derivative compound be administered with other products that potentiate the activity of the peptide, including the antifungal activity of the peptides. For example, serum complement potentiates the gram-negative bactericidal activity of BPI protein products; the combination of BPI protein product and serum complement provides synergistic bactericidal/growth inhibitory effects. See, e.g., Ooi et al., 1990, *J. Biol. Chem.* 265: 15956 and Levy et al., 1993, *J. Biol. Chem.* 268: 6038–6083 which address naturally-occurring 15 kD proteins potentiating BPI antibacterial activity. See also co-owned, co-pending PCT Application No. US94/07834 [WO 95/02414], which corresponds to U.S. Pat. No. 5,770,561 which describe methods for potentiating gram-negative bactericidal activity of BPI protein products by administering lipopolysaccharide binding protein (LBP) and LBP protein products. LBP protein derivatives and derivative hybrids which lack CD-14 immunostimulatory properties are described in PCT Application No. US94/06931 [WO 95/00641], which corresponds to co-owned U.S. Pat. No. 5,731,415. It has also been observed that poloxamer surfactants enhance the anti-bacterial activity of BPI protein products, as described in Lambert, U.S. Pat. No. 5,912,228; poloxamer surfactants may also enhance the activity of antifungal agents.

Without being bound by a theory of the invention, it is believed that derivative compounds of the invention may have several modes of action. The compound, through its heparin-binding ability, may interfere with the binding of fungi to the extracellular matrix. For example, heparin-like surface molecules of Candida are believed to mediate adhesion of the yeast to extracellular matrix and host tissues. The compound may also act directly on the cytoplasmic membrane of fungi. In addition, the compound may bind to fungal cell wall mannoproteins that are structurally similar to the LPS of gram-negative organisms or that are responsible for adherence to target host tissues, thus interfering with fungal interaction with host tissues. Binding to fungal mannans may also promote access of the peptide to the inner cytoplasmic membrane. In addition, because fungal infection may cause stress-induced translocation of bowel flora and/or LPS, the compound may also act beneficially by killing gram-negative bacteria and neutralizing LPS. Finally, the antifungal activity of compound according to the invention may result from unique structural features. For example, a six amino acid sequence within Domain III [WLIQLF (SEQ ID NO: 59)] and the included five and four amino acid sequences [LIQL (SEQ ID NO: 55), IQLF (SEQ ID NO: 56), WLIQL (SEQ ID NO: 57), LIQLF (SEQ ID NO: 58)] are composed of hydrophobic amino acids with the exception of glutamine (Q) that is a neutral hydrophilic amino acid. This hydrophobic stretch is bounded by highly cationic (polar) lysines on the N- and C-termini. This motif is reminiscent of leader/signal peptides as well as transmembrane segments of membrane proteins. Aliphatic amino acids such as I, L, V, M, A, have a high propensity to form transmembrane α-helical structures within the hydrophobic membrane environment when found in sequences of 12–15 nonpolar amino acids due to their ability to form backbone hydrogen bonds. Aromatic hydrophobic amino acids such as W and F can also incorporate into a membrane α-helix. The neutral, hydrophilic glutamine in the middle of a Domain III hydrophobic stretch may participate in hydrogen bonding with other fungal membrane components such as ergosterol and thus play an important role in the fungicidal activity. A short 10 Domain III derived amino acid peptide is not expected to be long enough to span a lipid bilayer and probably has a much different mechanism of action than a membrane disrupting, amphipathic type of cationic antimicrobial peptide. The short motif of six to twelve amino acid peptides with a core of neutral amino acids bounded by cationic amino acids is not long enough to span a fiugal lipid bilayer and thus may be allowed to traverse the membrane bilayer more efficiently than longer peptides. If transported inside the cell, the cationic/neutral/cationic molecules may inhibit the function of endogenous polyamines (spermidine, spermine, putrescine) by either competitive inhibition of the polyamine regulation of cell wall carbohydrate synthesis and/or by feedback inhibition of polyamine synthesis.

In addition, the invention provides a method of killing or inhibiting growth of fungi comprising contacting the fungi with a derivative compound according to the invention. This method can be practiced in vivo or in a variety of in vitro uses such as use in food preparations or to decontaminate fluids and surfaces or to sterilize surgical and other medical equipment and implantable devices, including prosthetic joints. These methods can also be used for in situ sterilization of indwelling invasive devices such as intravenous lines and catheters, which are often foci of infection.

A further aspect of the invention involves use of a derivative compound according to the invention for the manufacture of a medicament for treatment of fungal infection. The medicament may include, in addition to such derivative compound, according to the invention, other chemotherapeutic agents such as antifungal agents. The medicament can optionally comprise a pharmaceutically acceptable diluent, adjuvant or carrier.

The administration of antifungal derivative compounds is suitably accomplished with a pharmaceutical composition comprising a derivative compound and a pharmaceutically acceptable diluent, adjuvant, or carrier. The derivative compound may be administered without or in conjunction with known surfactants, other chemotherapeutic agents or additional known antifungal agents.

Other aspects and advantages of the present invention will be understood upon consideration of the following illustrative examples wherein Example 1 addresses peptide preparation and purification; Example 2 addresses in vitro antifungal testing of peptides; Example 3 addresses additional in vitro and in vivo testing of the antifungal effect of peptides on a variety of fungal species, including Candida strains and antibiotic resistant strains; Example 4 addresses the in vivo effect of peptides on survival of mice challenged with Candida; Example 5 addresses the serum stability of peptides; Example 6 addresses the design and assay of antifungal peptides for structural motif and minimum functional sequence analysis; Example 7 addresses LPS neutralization activities of antifungal peptides; and Example 8 addresses peptide formulations.

Synthetic peptides derived from Domain III of BPI have demonstrated potent antifungal, as well as antibacterial, activity towards a wide spectrum of microorganisms by radial diffusion and broth microdilution assays. For example, XMP.365, an all-D decapeptide derived from Domain III of BPI, has good antimicrobial activities with an MIC range of 0.16 to 2 μg/mL against *Candida albicans,* and 4–8 μg/mL against *Staphylococcus aureus.* However, this decamer construct when tested through the epithelial cell screening assays with MDCK and CACO-2 cells exhibited little or no mobility (0.05 to 0.06%). The present invention provides a series of derivative compounds based on subsequences of Domain III of BPI which exhibit enhanced cellular uptake, lumenal absorption, and bioavailability, while still retaining potent antifungal activity. Preferred derivatives according to the invention exhibit enhanced bioavailability when introduced via orally administered routes.

A series of chemically derivatized peptide-based constructs based on XMP.365 are provided with retained and/or enhanced antifungal activity and preferably with increased oral absorption. To this end, XMP.365 was prepared through solid support chemistry, utilizing an orthogonal protection scheme. Various organic carboxylic acids were anchored onto N-terminus or ε-amine of lysines using coupling reagents HBU or DIPCDI. These derivatized sequences were then synthesized and purified. Such derivative compounds may be prepared according to a variety of know and conventional synthesis procedures and the following examples are not meant to be exhaustive. All such means of synthesizing and purifying the derivatized peptides are contemplated by the present invention.

After obtaining the derivatized compounds, they were screened for increased absorption and a retention of antimicrobial, particularly antifungal, activity. In vitro absorption and oral availability is tested via screening assays with MDCK and CACO-2 cells, while antimicrobial activity is tested via radial diffusion and broth microdilution assays. The results from these studies indicate that derivative compounds with antifungal activity based on subsequences derived from Domain III of BPI can be prepared with increased epithelial cell transfer. For example, XMP.560, a derivative of XMP.365, afforded an MIC value of 2 μg/mL against *Candida albicans* SLU1, and increased cell absorption to 2% in MDCK cell screening assays. The present invention discloses that positions of chemical modification, as well as the nature of the functional groups, are important parameters of increasing cellular transfer. Successful modifications learned from these studies can be applied to other bioactive constructs to increase oral bioavailability.

EXAMPLE 1

Derivatized Peptide Synthesis and Purification

This example addresses the preparation and purification of derivative compounds that are peptide-based constructs according to the invention.

Peptide-based constructs may be prepared according to a variety of synthetic procedures. For example, BPI-derived peptides have been prepared by solid phase peptide synthesis as described in co-assigned U.S. patent application Ser. No. 08/183,222 filed Jan. 14, 1994 (abandoned) and U.S. Pat. No. 5,733,872, according to the methods of Merrifield, J. Am Chem. Soc. 85: 2149 (1963) and Merrifield et al. Anal. Chem., 38: 1905–1914 (1966) using an Applied Biosystems, Inc. Model 432 peptide synthesizer.

Alternatively, BPI-derived peptides have been synthesized on a larger scale using solid phase peptide synthesis on an Advanced Chemtech (ACT-Model 357 MPS) synthesizer utilizing a 1-Fluorenylnethyl-oxycarbonyl (Fmoc) protection strategy with a double coupling procedure employing N,N-diisopropylcarbodiimide (DIC)/1-hydroxybenzotriazole (HOBt) and 2-(1-H-benzotiazol-1-yl)-1,1,3,3,-tetramethyluronium hexa-fluorophosphate (HBTU)/HOBt/diisopropylethylamine (DIEA) as described in U.S. Pat. No. 5,858,974 and herein.

The solid support used in the synthesis of peptide-based constructs of the present invention was a polystyrene resin with 1% divinylbenzene (DVB) cross-linking and an 4-(2', 4'-dimethoxyphenyl-Fmoc-aminomethyl)-phenoxy (Fmoc-Rink amide) linker with a substitution rate of 0.56 mmoles/gram. A scale between 0.1 grams and 5 grams of starting resin may be used, and was generally 0.25 grams for the synthetic peptide-based constructs described herein.

For such syntheses, dimethylformamide (DMF) was the primary solvent with a 50/50 solution of piperidine/DMF used for Fmoc deprotection in three consecutive treatments of 1, 5, and 10 minutes, respectively. A double coupling procedure was used in each cycle with a 4:1 amino acid to peptide ratio used in each coupling. The amino acids were dissolved in a 0.5M HOBt solution in N-methylpyrrolidinone (NMP) at a concentration also of 0.5M. For the first coupling, an equimolar (to amino acid) amount of a 0.5M solution of diisopropylcarbodiimide (DIPCDI) in NMP was used and allowed to react for 45 minutes. The second coupling utilized an equimolar (to amino acid) volume of a 0.5M HBTU solution in DMF with an equal volume of a 1M DIEA solution in NMP (2:1, DIEA:amino acid) for a period of 30 minutes.

Upon completion of the synthesis, the resin was treated with MeOH, dried under reduced pressure, and then cleaved using a cocktail composed of trifluoroacetic acid (TFA) :thioanisole:ethanedithiol (EDT):water, at a ratio of 36:2:1:1 (with the volume dependent on the amount of resin) for 2 hours (a minimum of 2 hours was used with an additional 30 minutes added for each arginine, but not exceeding 3 hours) with the first 15 minutes occurring in a wet ice bath. The solutions were then dissolved in a 10% TFA in water solution, washed 3 times with methyl t-butyl ether (MTBE) and lyophilized.

The amino termini of selected peptide-based constructs or selected R groups may be derivatized, for example, with acetic anhydride or other organic carboxylic acid after synthesis on solid phase using an N-terminal Fmoc protection strategy as described above. Subsequent to Fmoc removal with piperidine and prior to peptide cleavage with TFA, peptide on the resin could be derivatized with a 5–10 fold molar excess of acetic anhydride or 4-fold molar excess of another R group such as an organic carboxylic acid with a 2-fold molar excess of diisopropylethylamine in dimethylformamide for one hour or a double coupling procedure employing N,N-diisopropylcarbodiimide (DIC)/1-hydroxybenzotriazole (HOBt) and 2-(1-H-benzotriazol-1-yl)-1.1.3.3.-tetramethyluronium hexa-fluorophosphate (HBTU)/HOBt/diisopropylethylamine (DIEA) and one of a variety of building blocks could be used for derivatization. The peptide was then cleaved from the resin with the TFA cleavage cocktail as described above and purified as described below. Derivatization, including N-terminal acetylation, of the purified peptide was verified by mass spectrometry.

Yields of the peptide-based constructs described in Table I ranged from 9 to 26%. All HPLC purities were generally greater than 90% and mass was construed by mass spectrometry.

For purity analysis of each newly synthesized peptide-based construct, dilute solutions of crude lyophilized peptide-based constructs were prepared and analyzed on a Michrom Ultrafast Microprotein Analyzer equipped with a 150 mm×1 mm, 5 µL particle, 300 Å pore C-8 Zorbax column. The column oven was set to 40° C., the flow rate was 100 µL/minute, and injection volumes were typically 5–10 µL. HPLC was performed using 5% acetonitrile/0.1% TFA in water as mobile phase A, and 80% acetonitrile/ 0.065% TFA as mobile phase B. The eluate was monitored spectrophotometrically at 214 nm. Percent purity was calculated from the peak area of the individual peptide constructs.

Selected constructs were purified by high performance liquid chromatography (HPLC), using a Waters Prep LC 2000 Preparative Chromatography System (Water Corp., Milford, Mass.) equipped with a Delta Pak C-18, 15 µm, 300 Å cartridge column consisting of a 40×10 mm guard cartridge and a 40×100 mm Prep Pak cartridge. The column was equilibrated in 25% buffer B, where A=5% acetonitrile/ 0.1% trifluoroacetic acid and B=80% acetonitrile/0.065% trifluoroacetic acid. Such peptide-based constructs were dissolved to ~20 mg/mL in buffer A and 200–800 mg were applied to the column through the LC pump operating at a flow rate of 8–17 mL/min. Bound material was eluted with a gradient of 40–55% buffer B/30 min applied at 8–17 mL/min. (Some constructs were purified with a gradient of 5–60% B/30 min.) The eluate was monitored at 220 and/or 280 and 300 nm with a Waters 490E Programmable Multiwavelength Detector. Fractions were collected and assayed for the construct of interest on an Ultrafast Micoprotein Analyzer (Michrom BioResources, Inc., Pleasanton, Calif.) equipped with a Zorbax C-8, 150×1 mm, 5 µm, 300 Å maintained at 40° C. Fractions containing the construct of interest at ≧90% purity were pooled and lyophilized to dryness. The purity of the recovered material was determined with analytical reverse-phase BPLC.

Table I, diagrammatically sets forth the full core peptide-based sequence, with locations of potential chemical derivatization, and a number of constructs that were synthesized, with their respective derivative moieties indicated, along with corresponding molecular weights.

TABLE I

Constructs†

$$R_1\text{-lys-trp-leu-ile-gln-leu-phe-his-lys-lys-NH}_2$$

with $R_3$ on position 10 lys, $R_2$ on position 9 lys, and arrow pointing to Position 1.

| Peptide-Based Construct | Derivatization | Mol. Wt. |
|---|---|---|
| XMP.365 (SEQ ID NO: 1) | $R_1 = R_2 = R_3 = H$ | 1339.7 |
| XMP.366 (SEQ ID NO: 2) | $R_1$ = acetyl, $R_2 = R_3 = H$ | 1381.7 |
| XMP.416 (SEQ ID NO: 3) | $R_1$ = 7-amino-heptylcarbonyl, $R_2 = R_3 = H$ | 1480.9 |
| XMP.496 (SEQ ID NO: 15) | $R_1$ = 10-amino-decylcarbonyl, $R_2 = R_3 = H$ | 1552.9 |
| XMP.499 (SEQ ID NO: 16) | $R_1$ = 2-pyrazine carbonyl, $R_2 = R_3 = H$ | 1445.8 |
| XMP.500 (SEQ ID NO: 17) | $R_1$ = 4-imidazole carbonyl, $R_2 = R_3 = H$ | 1433.8 |
| XMP.501 (SEQ ID NO: 18) | $R_1$ = 1-(4-imidazole) methylene carbonyl, $R_2 = R_3 = H$ | 1447.8 |
| XMP.502 (SEQ ID NO: 19) | $R_1$ = 2-imino-1-imidazolidine methylene carbonyl, $R_2 = R_3 = H$ | 1463.8 |
| XMP.503 (SEQ ID NO: 20) | $R_1$ = pyridine carbonyl, $R_2 = R_3 = H$ | 1444.8 |
| XMP.504 (SEQ ID NO: 21) | $R_1$ = 3-piperidine carbonyl, $R_2 = R_3 = H$ | 1450.8 |
| XMP.518 (SEQ ID NO: 24) | $R_1$ = acetyl, $R_2 = H$, $R_3$ = biotin-carbonyl | 1608.1 |
| XMP.519 (SEQ ID NO: 25) | $R_1$ = biotin-carbonyl, $R_2 = R_3 = H$ | 1580.0 |
| XMP.521 (SEQ ID NO: 27) | $R_1$ = acetyl, $R_2$ = biotin-carbonyl, $R_3 = H$ | 1680.1 |
| XMP.533 (SEQ ID NO: 35) | $R_1$ = 2-quinoxal carbonyl, $R_2 = R_3 = H$ | 1497.0 |
| XMP.534 (SEQ ID NO: 36) | $R_1$ = biphenylene-carbonyl, $R_2 = R_3 = H$ | 1517.9 |
| XMP.536 (SEQ ID NO: 38) | $R_1$ = benzofuran-carbonyl, $R_2 = R_3 = H$ | 1483.8 |
| XMP.545 (SEQ ID NO: 39) | $R_1$ = indole-carbonyl, $R_2 = R_3 = H$ | 1482.8 |
| XMP.546 (SEQ ID NO: 40) | $R_1$ = 1-isoquinoline-carbonyl, $R_2 = R_3 = H$ | 1496.1 |
| XMP.560 (SEQ ID NO: 41) | $R_1$ = salicylic-carbonyl, $R_2 = R_3 = H$ | 1460.0 |
| XMP.596 (SEQ ID NO: 43) | $R_1$ = quinaldic-carbonyl, $R_2 = R_3 = H$ | 1495.2 |
| XMP.618 (SEQ ID NO: 48) | $R_1$ = 2-nitro-3-chloro-benzoyl, $R_2 = R_3 = H$ | 1522.6 |

†$R_1$ is optionally modified on the α-amine of the position 1 residue. $R_2$ and/or $R_3$ are optionally modified on the ε-amine of the position 9 lysine and position 10 lysine, respectively.

EXAMPLE 2

In Vitro Antifungal Effects

This example addresses in vitro screening of derivatized compounds based on peptide sequences derived from Domain III of BPI for antifungal activity via a broth microdilution assay and a radial diffusion assay.

Table II below sets out constructs derived from or based on Domain III BPI sequences, including derivative compounds. Such constructs may be identified by number with a prefix XMP or BPI (e.g. XMP.1 or BPI.1, XMP.2 or BPI.2, etc.). Table II also sets out the derivatization for each construct tested.

In each broth microdilution assay screening procedure, a colony of *Candida albicans* designated CA-1, Strain SLU-1 that was received from the laboratories of G. Matuschak and A. Lechner, St. Louis University Hospital, St. Louis, Mo., where the strain was maintained, was inoculated into a tube containing 5 mL Sabouraud Dextrose broth (2% dextrose, 1% neopeptone) and incubated at 37° C. with shaking. The overnight culture was diluted 1:50 into 5 ml of fresh broth and incubated for 3 hours at 37° C. to exponential phase growth. Organisms were pelleted by centrifugation in a Beckman J-6M centrifuge for 5 minutes at 3000 rpm (1500× g) and the pellets were resuspended in 5 mL phosphate buffered saline (PBS) and the optical density (OD) at 570 nm was determined. On the basis of the determination that one OD unit equals $3 \times 10^7$ colony forming units/mL (CFU/mL), yeast cells were diluted to $5 \times 10^3$ CFU/mL in Sabouraud Dextrose broth (SBD).

Derivatized peptide sequences based on Domain III of BPI to be screened which were originally constituted in Dulbecco's-PBS, were two-fold serially diluted in SDB starting from a concentration of 128 μg/mL. Equal volumes (100 μL) of yeast suspension as prepared above and derivatized peptide solution were added to wells of a 96-well sterile, flat bottom, non-pyrogenic tissue culture microtiter plate (Costar, Cambridge, Mass.) to reach a final volume of 200 μL/well. The plate was incubated on a shaker at 37° C. for 24 hours. All assays were performed in triplicate. Following the incubation period, plates were read in an ELISA plate reader at 595 nm wavelength to determine the minimum inhibitory concentration (MIC), i.e., the lowest concentration required to reduce the optical density at 595 nm to below 0.1 OD. The MIC (μg/mL) of each derivatized peptide construct for *C. albicans* SLU1 (CA-1) is set forth in Table II.

In the radial diffusion assay procedures, the CA-1 cultures and derivatized peptide solutions were prepared as in the broth microdilution assay procedure described above, i.e., CA-1 was grown to exponential phase in SDB. Ten (10) mL of molten underlayer agarose comprising 3% Sabouraud Dextrose broth, 1% agarose (Pharmacia, Piscataway, N.J.), 0.02% Tween 20, and 10 mM sodium phosphate at pH 7.4, was added to polystyrene tubes and maintained in a 56° C. water bath until the addition of yeast. Tubes were cooled to approximately 45° C., yeast were added to give a final concentration of $1 \times 10^6$ CFU/mL, and the tubes were mixed again by inverting. The contents were poured into leveled, square petri dishes and distributed evenly. The agarose solidified in less than 30 seconds and had a uniform thickness of about 1 mm. A series of wells were punched into the hardened agarose using a sterile 3 mm punch attached to a vacuum apparatus to achieve a uniform, 3 mm diameter well.

Derivatized peptide sequences to be assayed were 2-fold serially diluted in 10 mM Dulbecco's PBS (D-PBS) starting from a concentration of approximately 1 mg/nL. Five μL of each dilution were added to each well and the plates were incubated at 37° C. for 3 hours to allow for complete diffusion of the test compounds. An overlayer of 10 mL of molten agarose comprising 6% Sabouraud Dextrose broth, 1% agarose, and 10 mM sodium phosphate, pH 7.4, (at approximately 45° C.) was then added and plates were incubated overnight at 37° C. Following this overnight incubation, a dilute Coomassie solution was poured into the plates and allowed to stain for 24 hours to enhance visualization of the zones.

Clear zones of growth inhibition around each well were measured with calipers. The actual area of growth inhibition ($mm^2$) was calculated by subtracting the area of the well. Table II below sets out the results of the radial diffusion assays for a series of tested peptide-based constructs in terms of the number of picomoles (pmol) of compound required to establish a 30 mm² area of growth inhibition of *Candida albicans* SLU-1 calculated by PROBIT analysis (e.g., calculated from regression of the linear portion of log-concentration dose-response curve, log pmol/well vs. net area of inhibition). These data demonstrate that all-D isomer peptide-based constructs with subsequences derived from Domain III of BPI can be chemically derivatized without significant loss of antifungal activity.

TABLE II

Compound Data from In Vitro Screening

| Peptide-Based Construct | Radial Diffusion (pmol to achieve 30 mm² zone C. albicans SLU1) | Broth Microdilution (MIC values in µg/mL C. albicans SLU1) |
| --- | --- | --- |
| XMP.365 | 285 | 2 |
| XMP.366 | 352 | 4 |
| XMP.416 | 410 | 1 |
| XMP.496 | 434 | 1 |
| XMP.518 | 484 | 8 |
| XMP.519 | 170 | 1 |
| XMP.521 | 959 | 16 |
| XMP.534 | >3,371 | 4 |
| XMP.535 | b | b |
| XMP.536 | >3,371 | 4 |
| XMP.545 | 1,635 | 8 |
| XMP.546 | >3,371 | >64 |
| XMP.560 | 451 | 2 |
| XMP.596 | 3,140 | 2 |
| XMP.618 | 2,146 | 4 | b - no detectable activity up to 5 µg/well

Additional peptide-based constructs with antifungal activity, including, for example, XMP.424 (SEQ ID NO: 4), XMP.446 (SEQ ID NO: 5), XMP.447 (SEQ ID NO: 6), XMP.459 (SEQ ID NO: 7), XMP.466 (SEQ ID NO: 8), XMP.475 (SEQ ID NO: 9), XMP.492 (SEQ ID NO: 13), XMP.493 (SEQ ID NO: 14), XMP.532 (SEQ ID NO: 34), XMP.565 (SEQ ID NO: 42), XMP.620 (SEQ ID NO: 49), XMP.642 (SEQ ID NO: 50), XMP.653 (SEQ ID NO: 51) and XMP.678 (SEQ ID NO: 52), are derivatized and tested according to procedures disclosed herein.

EXAMPLE 3

In Vivo Antifungal Activity

This example addresses the in vivo antifungal activity of the chemically derivatized, all-D isomer peptide sequences based on Domain III of BPI.

Derivatized peptide-based constructs are tested for activity upon oral administration (oral activity) in a 28-day comparative survival efficacy study in mice systemically infected with *Candida albicans*. Specifically, male DBA/2 mice (Charles River Laboratories) six weeks of age are dosed with $7.9 \times 10^4$ *Candida albicans*, SLU-1 in 100 µL intravenously via the tail vein in a single dosage on day zero (0). However, other routes of administration, including intraperitoneal (ip) and subcutaneous (sc) routes may be administered. Amphotericin B will provide complete protection at 0.5 mg/kg qod (100% survival). Mortality data will be subjected to Kaplan-Meier survival analysis. All treatment groups may be considered statistically significant vs. saline at p values <0.05.

Treatment begins immediately thereafter with 400 µL oral gavage of either 0.5% dextrose, or derivative compound in 0.5% dextrose at various dosage levels (e.g., 10 mg/kg or 20 mg/kg) according to a prescribed dosing regimen (e.g. every other day for a total of eight times). Amphotericin B (Fungizone®) is administered intravenously at 0.5 mg/kg as a positive control every other day for a total of eight times. Twice-day monitoring (once daily on weekends and holidays) for mortality is performed. The animals treated with antifungal derivative compound show improvement in mortality compared with the dextrose-treated controls, preferably statistically significant improvement (p-value of <0.5). At two doses less than 5 mg/kg, XMP.496 (SEQ ID NO: 15), XMP.500 (SEQ ID NO: 17), XMP.503 (SEQ ID NO: 20), XMP.519 (SEQ ID NO: 25), XMP.534 (SEQ ID NO: 36), and XMP.560 (SEQ ID NO: 41) did not exhibit statistically significant improvement in initial experiments (p>0.5).

EXAMPLE 4

In Vitro Oral Absorption Screening

This example addresses the activity of peptide-based constructs in in vitro transport screening assays.

For these experiments, peptide-based constructs are screened for potential oral absorption in in vitro screening assays using MDCK and/or CACO-2 cells. Briefly, cultured monolayers of Madin-Derby canine kidney epithelial (MDCK) cells (ATCC Accession No. CCL-34) and/or CACO-2 (Human colon carcinoma) cells [Audus, K. L., et al. *Phar. Res.*, 7:435–451 (1990) are grown upon collagen-coated, permeable-filter supports (Becton Dickinson, Mountain View, Calif.). The cells are grown to confluency and allowed to differentiate (e.g., about 3 days for MDCK cells or about 21 days for CACO-2 cells). The integrity of the monolayers is determined by measuring the transepithelial resistance. The cells are incubated with a peptide-based construct on the apical side for 2.5 hours in MDCK or CACO-2 screening. The transepithelial transport of the construct is measured by quantitative HPLC analysis of the incubation media on the basolateral side of the cells (forward transport). Radiolabelled mannitol and/or cortisone are used as positive controls. In addition, the efflux of the construct is measured by quantitative HLPC analysis of the incubation media on the apical side of the cells. This follows incubation of the cells with construct on the basolateral side for 2.5 hours.

Details of the experimental procedures were as follows: MDCK or CACO-2 cells are grown to ~90% confluency in T75 tissue culture flasks in cell growth media (for MDCK cells, Minimum Essential Medium (Eagle's) GIBCO (Grand Island, N.Y.) #11095-080 or for CACO-2 cells, DMEM, GIBCO #11965-050, high glucose—500 mL; FBS 10% (Hyclone) heat treated—50 mL; L-Glutamine (200 mM) GIBCO #25030-016—5 mL; for CACO-2 cells, Non-essential amino acids, GIBCO #11140-050 (200 mM, 100x)—5.5 mL; and Penicillin/Streptomycin (100 µg/mL) GIBCO #15140-015—5 mL, that has been filtered and stored at 4° C.). The cells are trypsinized (~20 minutes for MDCK cells for passaging due to their tight adherence) and seeded on 24.5 mm transwells (Transwell-COL, #3245, Corning CoStar Corp., Cambridge, Mass.) at a concentration of ~$3 \times 10^6$ MDCK cells/well or ~$3 \times 10^5$ CACO-2 cells/well. For the MDCK cells, media is changed one day post seeding and the MDCK cells are allowed to grow for an additional 2 days. For the CACO-2 cells, media is changed every 2 days post seeding and the CACO-2 cells are allowed to grow for a total of up to 21 days.

Following the days post seeding, the cells are ready for transport experiments. The cells are fed fresh media 2 hours before starting the transport experiment. The cells are then washed with transport media (TM: Hank's Balanced Salt Solution (HBSS) GIBCO #14025-027, with no phenol red; 10 mM HEPES (from 1 M HEPES) GIBCO #15630-015, pH balanced with NaOH to 7.4) and placed in new 6 well plates. Donor solutions of peptide-based constructs for assay are prepared in 1.5 mL TM at a concentration of ~100 μg/mL. For forward transport studies, these 1.5 mL construct solutions are added to the apical chamber of the transwells. Approximately 2.6 mL of acceptor solution (TM only, no construct) is added to the basolateral chamber. For efflux studies, the donor solution with construct is added to the basolateral chamber and acceptor solution (TM only, no construct) is added to the apical chamber. Each construct is assayed at least in triplicate.

The transwells are returned to the 37° C. tissue culture incubator for 2.5 hours. At the end of 2.5 hours the apical and basolateral solutions are separately freeze dried (lyophilized) in high vacuum in 15 mL conical tubes. The samples are then resuspended in 200 μL HPLC buffer A (5% acetonitrile: 95% water: 0.1% tetrafluoroacefic acid (TFA)) and 50 μL of the resuspended sample is used for HPLC analysis.

Apical control wells containing 1.5 mL TM with tritiated mannitol ($^3$H-mannitol, 1 μCi/mL; Dupont NEN Research Products, #NET-101, Boston, Mass.) are analyzed separately for counts per minute (cpm) of tritium to test the integrity of the MDCK cell monolayers.

Forward transport is calculated as the percentage of peptide-based construct in the basolateral chamber (determined by the area under the HPLC peak) to the initial concentration of the apical solution (initial donor concentration of ~100 μg/mL). For efflux experiments, the reverse calculation is made (percentage of peptide-based construct in the apical chamber to the initial construct concentration in the basolateral solution). Such intestinal absorption screening identifies constructs that are potential orally available compounds. Results of forward flow and efflux for a number of peptide-based constructs from the in vitro oral absorption screening with MDCK cells are shown in Table III.

TABLE III

| In Vitro Oral Availablity Screening (%) | | |
|---|---|---|
| Construct | Forward | Efflux |
| XMP.365 | 0.03 | 0 |
| XMP.366 | 0 | 0 |
| XMP.416 | 0.55 | 0.46 |
| XMP.496 | 1.04 | 0.45 |
| XMP.519 | 0 | ND |
| XMP.534 | ≧2 | ≧2 |
| XMP.535 | 0.29 | 0.29 |
| XMP.536 | 0 | 0.23 |
| XMP.545 | 0.41 | 1.54 |
| XMP.546 | 0 | 0 |
| XMP.560 | ≧2 | ≧2 |
| XMP.596 | 0 | 0 |
| XMP.618 | 0 | 1.4 |

ND = not determined

EXAMPLE 5

In Vivo Oral Absorption Screening

This example addresses the activity of peptide-based constructs for oral absorption in an in vivo screening assay in which constructs are administered by oral gavage to mice.

Briefly, serum concentrations of the constructs are measured at various time intervals after administration by HPLC. For example, constructs may be administered to mice at various dosages (e.g., 10 mg/kg body weight or 20 mg/kg body weight) and serum peptide concentrations are measured at various time intervals (e.g., 1 hours, 4 hours, and/or 24 hours) after administration to the mice. HPLC analysis identifies constructs that are absorbed after oral administration. Such constructs showing increased oral availability may achieve therapeutically effective serum concentrations after oral administration.

Other peptide-based constructs are described in concurrently filed U.S. application Ser. No. 09/344,219 and U.S. application Ser. No. 09/344,827 and are hereby incorporated by reference in their entirety. All U.S. patents, U.S. patent applications, PCT Publications and references cited herein are hereby incorporated by reference in their entirety. Numerous modifications and variations of the above-described invention are expected to occur to those of skill in the art. Accordingly, only such limitations as appear in the appended claims should be placed thereon.

What is claimed is:

1. A compound with antifungal properties comprising a sequence having the formula:

$$R_1\text{-leu-ile-gln-leu-}R_2 \text{ (SEQ ID NO: 60)}$$

wherein, $R_1$ is selected from the group consisting of $R_3$—, $R_3$-α-, and $R_3$-α-χ-;

$R_3$ is selected from the group consisting of $R_4$—$CH_2$—, $R_4$—$CH_2$—CO—, $R_4$—CO—, $R_4$—$SO_y$—, and $R_4$—$PO_z$—; wherein, y=0–3, z=1–4;

$R_4$ is a hydrophobic moiety selected from the group consisting of a cyclic molecule having at least 3 carbon atoms, a heterocyclic molecule having at least 3 atoms, a functionalized cyclic molecule having at least 3 carbon atoms, and a functionalized heterocyclic molecule having at least three atoms;

wherein said $R_4$ is a hydrophobic moiety selected from the group consisting of biotin, 2-biphenylene, 2-anthraquinone, 2-benzofuran, 2-indole, 1-isoquinoline, hydroxyphenyl, 2-quinoline, 1-(3-(3,4-dihydroxycinnamoyl)-1,3,4,5-tetrahydroxycyclohexane), 1-(3,5-dichloro-2-hydroxyphenyl), 1-(3,5-diiodo-2-hydroxyphenyl), 1-(3,5-dinitro-2-hydroxyphenyl), 1-(4-azido-2-hydroxyphenyl), 4-biphenyl, 2-biphenyl, 1-naphthyl, 2-naphthyl, 3-amino-2-naphthyl, 3-chloro-2-nitrophenyl, (3,4-dihydroxyphenyl), 3,4,5-trihydroxyphenyl, 2-chloro-3-nitrophenyl, 5-azido-2-nitrophenyl, 3-amino-2-pyrazine, 2-benzyloxycarbonyl-ethyl, 2-thiophene, 2-(3,4-dihydroxyphenyl)ethene, 5-bromo-3-indolemethylene, 2-(4-hydroxy-3-methoxyphenyl)ethene, 2-(3-chlorophenyl)ethene, 2-pyrazine, 4-imidazole, 2-imino-1-imidazolidine, pyridine, 3-piperidine, 4-piperidine, fluorescein, 2-(4-amino-3,5,6-trichloropyridine), and 3-(2-chloro-6-fluorophenyl)-5-methylisoxazole;

α is a hydrophilic basic amino acid moiety selected from the group consisting of lysine, arginine, histidine, ornithine, diaminobutyric acid, citrulline, and para-amino phenylalanine;

χ is a hydrophobic amino acid moiety selected from the group consisting of alanine, naphthylalanine, biphenylalanine, valine, leucine, isoleucine, proline, hydroxyproline, phenylalanine, tryptophan, methionine, glycine, cyclohexylalanine, amino-isobutyric acid, norvaline, norleucine, tert-leucine, tetrahydroisoquinoline, pipecolic acid, phenylglycine, homophenylalanine, cyclohexylglycine, dehydroleucine, 2,2-diethylglycine, 1-amino-1-cyclopentane carboxylic acid, 1-amino-1-cyclohexane carboxylic acid, 2-amino-1-benzene carboxylic acid, 3-amino-1-benzene carboxylic acid, 3-amino-2-naphthene carboxylic acid, γ-amino butyric acid, β-alanine, difluorophenylalanine, para-fluorophenylaniline, nipecotic acid, amino butyric acid, thienyl-alanine, and t-butyl-glycine;

R₂ is selected from the group consisting of —NH₂, -χ-NH₂, -χ-α-NH₂, -χ-α-α-NH₂, -χ-α-α-α-NH₂,

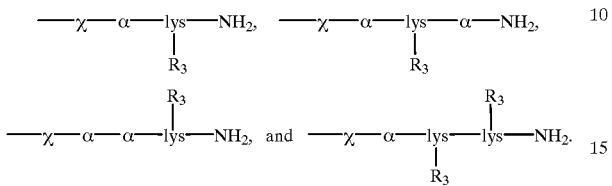

2. A compound with antifungal properties comprising a sequence having the formula:

R₁-ile-gln-leu-phe-R₂ (SEQ ID NO: 61)

wherein,

R₁ is selected from the group consisting of R₃—, R₃-α-, R₃-α-χ-, and R₃-α-χ-χ-;

R₃ is selected from the group consisting of R₄—CH₂—, R₄—CH₂—CO—, R₄—CO—, R₄—SO_y—, and R₄—PO_z—; wherein, y=0–3, z=1–4;

R₄ is a hydrophobic moiety selected from the group consisting of a cyclic molecule having at least 3 carbon atoms, a heterocyclic molecule having at least 3 atoms, a functionalized cyclic molecule having at least 3 carbon atoms, and a functionalized heterocyclic molecule having at least three atoms;

wherein said R₄ is a hydrophobic moiety selected from the group consisting of biotin, 2-biphenylene, 2-anthraquinone, 2-benzofuran, 2-indole, 1-isoquinoline, hydroxyphenyl, 2-quinoline, 1-(3-(3,4-dihydroxycinnamoyl)-1,3,4,5-tetrahydroxycyclohexane), 1-(3,5-dichloro-2-hydroxyphenyl), 1-(3,5-diiodo-2-hydroxyphenyl), 1-(3,5-dinitro-2-hydroxyphenyl), 1-(4-azido-2-hydroxyphenyl), 4-biphenyl, 2-biphenyl, 1-naphthyl, 2-naphthyl, 3-amino-2-naphthyl, 3-chloro-2-nitrophenyl, (3,4-dihydroxyphenyl), 3,4,5-trihydroxyphenyl, 2-chloro-3-nitrophenyl, 5-azido-2-nitrophenyl, 3-amino-2-pyrazine, 2-benzyloxycarbonyl-ethyl, 2-thiophene, 2-(3,4-dihydroxyphenyl)ethene, 5-bromo-3-indolemethylene, 2-(4-hydroxy-3-methoxyphenyl)ethene, 2-(3-chlorophenyl)ethene, 2-pyrazine, 4-imidazole, 2-imino-1-imidazolidine, pyridine, 3-piperidine, 4-piperidine, fluorescein, 2-(4-amino-3,5,6-trichloropyridine), and 3-(2-chloro-6-fluorophenyl)-5-methylisoxazole;

α is a hydrophilic basic amino acid moiety selected from the group consisting of lysine, arginine, histidine, ornithine, diaminobutyric acid, citrulline, and para-amino phenylalanine;

χ is a hydrophobic amino acid moiety selected from the group consisting of alanine, naphthylalanine, biphenylalanine, valine, leucine, isoleucine, proline, hydroxyproline, phenylalanine, tryptophan, methionine, glycine, cyclohexylalanine, amino-isobutyric acid, norvaline, norleucine, tert-leucine, tetrahydroisoquinoline, pipecolic acid, phenylglycine, homophenylalanine, cyclohexylglycine, dehydroleucine, 2,2-diethylglycine, 1-amino-1-cyclopentane carboxylic acid, 1-amino-1-cyclohexane carboxylic acid, 2-amino-1-benzene carboxylic acid, 3-amino-1-benzene carboxylic acid, 3-amino-2-naphthene carboxylic acid, γ-amino butyric acid, β-alanine, difluorophenylalanine, para-fluorophenylaniline, nipecotic acid, amino butyric acid, thienyl-alanine, and t-butyl-glycine;

R₂ is selected from the group consisting of —NH₂, -α-NH₂, -α-α-NH₂, -α-α-α-NH₂,

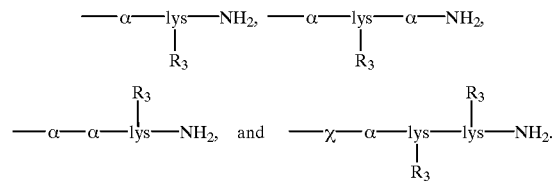

3. A compound selected from the group consisting of peptides of SEQ ID NOS: 1 through 52.

4. A pharmaceutical composition comprising the compound of any one of claim 1, 2 or 3 and a pharmaceutically acceptable diluent.

5. The pharmaceutical composition of claim 4 wherein said composition is for oral administration.

6. The pharmaceutical composition of claim 4 wherein said composition is for topical administration.

7. The pharmaceutical composition of claim 4 wherein said composition is for ophthalmic administration.

8. The pharmaceutical composition of claim 4 wherein said composition has antimicrobial activity.

9. The pharmaceutical composition of claim 4 wherein said composition has activity against gram-positive bacteria.

10. The pharmaceutical composition of claim 4 wherein said composition has antifungal activity.

11. The pharmaceutical composition of claim 4 wherein said composition has an epithelial absorption of at least 0.001%.

12. A method of treating a subject suffering from a fungal infection comprising the step of administering to said subject a therapeutically effective amount of the pharmaceutical composition of claim 4.

13. The method of claim 12 wherein said fungal infection involves infection by a fungal species selected from the group consisting of Candida, Aspergillus, Cryptococcus, Histoplasma, Coccidioides, Blastomyces, Basidiobolus, Conidiobolus, Rhizopus, Rhizomucor, Mucor, Absidia, Mortierella, Cunninghamella, Saksenaea, Fusarium, Trichophyton, Trichosporon, Microsporum, Epidermophyton, Scytalidium. Malassezia, Actinomyceies, Sporothrix and Penicillium.

14. A method of treating an immunocompromised subject comprising the step of administering to said subject an amount of the pharmaceutical composition of claim 4 effective to kill or inhibit replication of fungi.

15. The method of claim 12 comprising the further step of concurrently administering another non-BPI-derived antifungal agent.

16. A method of killing or inhibiting replication of fungi comprising the step of contacting said fungi with a compound of any one of claim 1, 2 or 3.

17. The method of claim 16 wherein said method is carried out in vitro.

* * * * *